(12) United States Patent
Román-Leshkov et al.

(10) Patent No.: US 11,179,708 B2
(45) Date of Patent: Nov. 23, 2021

(54) COMPOSITIONS AND METHODS FOR SELECTIVE CARBONYLATION OF HETEROCYCLIC COMPOUNDS

(71) Applicant: Massachusetts Institute of Technology, Cambridge, MA (US)

(72) Inventors: Yuriy Román-Leshkov, Cambridge, MA (US); Mircea Dinca, Belmont, MA (US); Hoyoung Park, Cambridge, MA (US)

(73) Assignee: Massachusetts Institute of Technology, Cambridge, MA (US)

( * ) Notice: Subject to any disclaimer, the term of this patent is extended or adjusted under 35 U.S.C. 154(b) by 36 days.

(21) Appl. No.: 16/339,688

(22) PCT Filed: Oct. 4, 2017

(86) PCT No.: PCT/US2017/055035
§ 371 (c)(1),
(2) Date: Apr. 4, 2019

(87) PCT Pub. No.: WO2018/067636
PCT Pub. Date: Apr. 12, 2018

(65) Prior Publication Data
US 2020/0164353 A1   May 28, 2020

Related U.S. Application Data

(60) Provisional application No. 62/403,938, filed on Oct. 4, 2016.

(51) Int. Cl.
| | | |
|---|---|---|
| *B01J 31/16* | (2006.01) | |
| *B01J 31/22* | (2006.01) | |
| *C07D 205/08* | (2006.01) | |
| *C07D 265/10* | (2006.01) | |
| *C07D 305/12* | (2006.01) | |
| *C07D 307/60* | (2006.01) | |

(52) U.S. Cl.
CPC ....... *B01J 31/1691* (2013.01); *B01J 31/2239* (2013.01); *C07D 205/08* (2013.01); *C07D 265/10* (2013.01); *C07D 305/12* (2013.01); *C07D 307/60* (2013.01); *B01J 2231/34* (2013.01); *B01J 2531/0216* (2013.01); *B01J 2531/62* (2013.01); *B01J 2531/845* (2013.01)

(58) Field of Classification Search
CPC .................................................. B01J 31/1691
See application file for complete search history.

(56) References Cited

U.S. PATENT DOCUMENTS

| | | | |
|---|---|---|---|
| 5,112,974 A | 5/1992 | Barton | |
| 6,893,564 B2 | 5/2005 | Mueller et al. | |
| 7,215,473 B2 | 5/2007 | Fleming | |
| 7,662,746 B2 | 2/2010 | Yaghi et al. | |
| 8,197,579 B2 | 6/2012 | Miller | |
| 8,372,779 B2 | 2/2013 | Schubert et al. | |
| 8,764,887 B2 | 7/2014 | Dinca et al. | |
| 9,758,532 B2 | 9/2017 | Dinca et al. | |
| 10,174,063 B2 | 1/2019 | Dinca et al. | |
| 10,442,875 B2 | 10/2019 | Dinca et al. | |
| 10,493,441 B2 | 12/2019 | Dinca et al. | |
| 2001/0003950 A1 | 6/2001 | Zhang et al. | |
| 2007/0171107 A1 | 7/2007 | Wang | |
| 2008/0188677 A1* | 8/2008 | Schubert ................. C07F 5/069 556/27 |
| 2008/0306315 A1 | 12/2008 | Lillerud et al. | |
| 2009/0221418 A1 | 9/2009 | Fischer et al. | |
| 2010/0069234 A1 | 3/2010 | Willis et al. | |
| 2010/0197990 A1 | 8/2010 | Schubert et al. | |
| 2010/0322837 A1 | 12/2010 | Miller | |
| 2011/0137100 A1 | 6/2011 | Toulhoat et al. | |
| 2011/0294658 A1 | 12/2011 | Lefevre et al. | |
| 2012/0077667 A1 | 3/2012 | Liu et al. | |
| 2012/0141685 A1 | 6/2012 | Gaab et al. | |
| 2012/0297982 A1 | 11/2012 | Dinca et al. | |
| 2013/0066128 A1 | 3/2013 | Breuil et al. | |
| 2013/0152789 A1 | 6/2013 | Polshettiwar et al. | |
| 2013/0204025 A1 | 8/2013 | Buso et al. | |
| 2014/0012039 A1 | 1/2014 | Yaghi et al. | |
| 2014/0326007 A1 | 11/2014 | Dinca et al. | |
| 2015/0047505 A1 | 2/2015 | Schroder et al. | |
| 2016/0046738 A1 | 2/2016 | Farha et al. | |
| 2016/0102040 A1 | 4/2016 | Allen et al. | |
| 2017/0073364 A1 | 3/2017 | Dinca et al. | |
| 2017/0341010 A1 | 11/2017 | Dinca et al. | |

(Continued)

FOREIGN PATENT DOCUMENTS

| | | | |
|---|---|---|---|
| CN | 104001476 B | 5/2016 | |
| WO | WO-03050154 A2 * | 6/2003 | ............ B01J 31/183 |

(Continued)

OTHER PUBLICATIONS

Church, T., et al. "A New Multicomponent Reaction Catalyzed by a [Lewis Acid]+[Co(CO)4]—Catalyst: Stereospecific Synthesis of 1,3-Oxazinane-2,4-diones from Epoxides, Isocyanates, and CO." J. Am. Chem. Soc. (2007), vol. 129, pp. 8156-8162. (Year: 2007).*
U.S. Appl. No. 16/240,629, filed Jan. 4, 2019, Dinca et al.
U.S. Appl. No. 15/760,104, filed Mar. 14, 2018, Dinca et al.
U.S. Appl. No. 15/760,122, filed Mar. 14, 2018, Dinca et al.
U.S. Appl. No. 15/607,255, filed May 26, 2017, Dinca et al.
PCT/US2017/055035, Jan. 18, 2018, International Search Report and Written Opinion.
PCT/US2017/055035, Apr. 18, 2019, International Preliminary Report on Patentability.
International Search Report and Written Opinion dated Jan. 18, 2018 for Application No. PCT/US2017/055035.

(Continued)

*Primary Examiner* — John S Kenyon
(74) *Attorney, Agent, or Firm* — Wolf, Greenfield & Sacks, P.C.

(57) ABSTRACT

Compositions comprising metal organic frameworks and related methods and uses are generally provided, including use in selective carbonylation of heterocyclic compounds.

13 Claims, 7 Drawing Sheets

(56) References Cited

U.S. PATENT DOCUMENTS

| | | | |
|---|---|---|---|
| 2018/0250664 | A1 | 9/2018 | Dinca et al. |
| 2018/0251581 | A1 | 9/2018 | Dinca et al. |
| 2019/0054446 | A1 | 2/2019 | Long et al. |
| 2019/0211043 | A1 | 7/2019 | Dinca et al. |

FOREIGN PATENT DOCUMENTS

| | | | | |
|---|---|---|---|---|
| WO | WO 2014/182648 | A1 | 11/2014 | |
| WO | WO 2015/142954 | A1 | 9/2015 | |
| WO | WO 2015/171791 | A1 | 11/2015 | |
| WO | WO-2015171791 | A1 * | 11/2015 | ............ C07F 15/045 |
| WO | WO 2017/048787 | A1 | 3/2017 | |
| WO | WO 2017/048795 | A1 | 3/2017 | |
| WO | WO 2015/171791 | A1 | 4/2018 | |
| WO | WO 2018/067636 | A1 | 4/2018 | |

OTHER PUBLICATIONS

International Preliminary Report on Patentability dated Apr. 18, 2019 for Application No. PCT/US2017/055035.
Church et al., A new multicomponent reaction catalyzed by a [Lewis Acid]$^+$[Co(CO)4]—Catalyst: Stereospecific Synthesis of 1,3-Oxazinane-2,4-diones from Epoxides, Isocyanates, and CO. J Am Chem Soc. Jun. 12, 2007;129(26):8156-62.
Park et al., Heterogeneous Epoxide Carbonylation by Cooperative Ion-Pair Catalysis in Co(CO)$_4$—Incorporated Cr-MIL-101. ACS Cent Sci. Mar. 21, 2017;3(5):444-8.
EP 17803667, Jan. 2, 2020, Partial European Search Report.
EP 17803667, Apr. 2, 2020, Partial European Search Report.
Abbenhuis, Heterogenization of Metallocene Catalysts for Alkene Polymerization. Angew. Chem. Int. Ed. 1999;38(8):1058-60.
Achmann et al., Metal-Organic Frameworks for Sensing Applications in the Gas Phase. Sensors. 2009;9(3):1574-89. Epub Mar. 6, 2009.
Akiyama et al., Effect of functional groups in MIL-101 on water sorption behavior. Microporous and Mesoporous Materials. 2012;157:89-93.
Alarco-Padilla et al., Application of absorption heat pumps to multi-effect distillation: a case study of solar desalination. Desalination. Jun. 25, 2007;212:294-302.
Al-Sa'Doun, Dimerization of ethylene to butene-1 catalyzed by Ti(OR')4-AlR3. Applied Catalysis A. Nov. 2, 1993;105(1):1-40.
Askalany et al., An overview on adsorption pairs for cooling. Renewable and Sustainable Energy Reviews. Mar. 2013;19:565-72.
Baier et al., Post-Metallocenes in the Industrial Production of Polyolefins. Ange. Chemie Int. Ed. Sep. 8, 2014;53(37):9722-44.
Bellarosa et al. When the Solvent Locks the Cage: Theoretical Insight into the Transmetalation of MOF-5 Lattices and Its Kinetic Limitations. Chem. Mater. 2015;27(9):3422-9. Epub Apr. 13, 2015.
Bertrand et al., Thiophene-based covalent organic frameworks. PNAS. Mar. 26, 2013; 110(13):4923-8. Epub Mar. 11, 2013.
Biswas et al., A cubic coordination framework constructed from benzobistriazolate ligands and zinc ions having selective gas sorption properties. Dalton Trans. 2009:6487-95. Epub Jun. 29, 2009.
Biswas et al., Homo- and Heteropentanuclear Coordination Compounds with Td Symmetry—the Solid State Structures of [MZn4(L)4(L')6] (M=CoII or Zn; L=chloride or acac; L'=1,2,3-benzotriazolate). Z. Anorg. Allg. Chem. Oct. 2008;634(14):2532-8.
Biswas et al., Syntheses and Magnetostructural Investigations on Kuratowski-Type Homo- and Heteropentanuclear Coordination Compounds [MZn4Cl4(L)6] (MII=Zn, Fe, Co, Ni, or Cu; L=5,6-Dimethyl-1,2,3-benzotriazolate) Represented by the Nonplanar K3,3 Graph. Inorg. Chem. 2010;49(16):7424-34. Epub Jul. 16, 2010.
Bonaccorsi et al., Hydrothermal and microwave synthesis of SAPO (CHA) zeolites on aluminum foams for heat pumping applications. Microporous and Mesoporous Mater. 2013;167:30-37.
Boudjouk et al., Solvated and Unsolvated Anhydrous Metal Chlorides from Metal Chloride Hydrates. Inorg. Synth. 1992;29:108-11.

Brozek et al., Cation exchange at the secondary building units of metal—organic frameworks. Chem. Soc. Rev. 2014;43:5456-67. Epub May 16, 2014.
Brozek et al., Dynamic DMF Binding in MOF-5 Enables the Formation of Metastable Cobalt-Substituted MOF-5 Analogues. ACS Cent. Sci. 2015;1(5):252-60. Epub Jul. 29, 2015.
Brozek et al., Lattice-imposed geometry in metal—organic frameworks: lacunary Zn4O clusters in MOF-5 serve as tripodal chelating ligands for Ni2+. Chemical Science. 2012;3:2110-3. Epub Apr. 4, 2012.
Brozfk et al., NO Disproportionation at a Mononuclear Site-Isolated Fe2+ Center in Fe2+-MOF-5. J. Am. Chem. Soc. 2015;137(23):7495-501. Epub May 19, 2015.
Brozfk et al., Solvent-Dependent Cation Exchange in Metal—Organic Frameworks. Chem. Eur. J. Jun. 2, 2014;20(23):6871-4.
Brozek et al., Ti3+−, V2+/3+−, Cr2+/3+−, Mn2+−, and Fe2+-Substituted MOF-5 and Redox Reactivity in Cr- and Fe-MOF-5. J. Am. Chem. Soc. 2013;135(34):12886-91. Epub Jul. 31, 2013.
Cadiau et al., Design of Hydrophilic Metal Organic Framework Water Adsorbents for Heat Reallocation. Adv. Mater. 2015;27:4775-80. Epub Aug. 26, 2015.
Campbell et al., Chemiresistive Sensor Arrays from Conductive 2D Metal—Organic Frameworks. J. Am. Chem. Soc. 2015;137(43):13780-3. Epub Oct. 11, 2015.
Campbell et al., Cu3(hexaiminotriphenylene)2: An Electrically Conductive 2D Metal—Organic Framework for Chemiresistive Sensing. Angewandte Chemie Int Ed. Mar. 27, 2015;54(14):4349-52. Epub Feb. 9, 2015. Supporting Information Included.
Canivet et al., MOF-Supported Selective Ethylene Dimerization Single-Site Catalysts through One-Pot Postsynthetic Modification. J. Am. Chem. Soc. 2013;135:4195-8. Epub Mar. 7, 2013.
Canivet et al., Structure—property relationships of water adsorption in metal—organic frameworks. New J. Chem. 2014;38:3102-11. Epub Apr. 16, 2014.
Canivet et al., Water adsorption in MOFs: fundamentals and applications. Chem. Soc. Rev. 2014;43:5594-617. Epub May 29, 2014.
Caskey et al., Dramatic tuning of carbon dioxide uptake via metal substitution in a coordination polymer with cylindrical pores. J Am Chem Soc. Aug. 20, 2008; 130(33):10870-1. doi: 10.1021/ja8036096. Epub Jul. 29, 2008.
Chen et al., Noncovalently Netted, Photoconductive Sheets with Extremely High Carrier Mobility and Conduction Anisotropy from Triphenylene-Fused Metal Trigon Conjugates. J Am Chem Soc. 2009; 131(21):7287-92. Epub May 4, 2009.
Chmiola et al., Anomalous Increase in Carbon Capacitance at Pore Sizes Less Than 1 Nanometer. Science. Sep. 22, 2006;313(5794):1760-3.
Chmiola et al., Desolvation of Ions in Subnanometer Pores and Its Effect on Capacitance and Double-Layer Theory. Angew. Chem. Int. Ed. Apr. 21, 2008;47(18):3392-5.
Choi et al., Broadly hysteretic H2 adsorption in the microporous metal-organic framework Co(1,4-benzenedipyrazolate). J Am Chem Soc. Jun. 25, 2008;130(25):7848-50. doi: 10.1021/ja8024092. Epub May 31, 2008.
Choi et al., Hydrogen storage in water-stable metal-organic frameworks incorporating 1,3 and 1,4 benzenedipyrazolate. Energy Environ Sci. 2010;3:117-23.
Choi et al., Supported Single-Site Catalysts for Slurry and Gas-Phase Olefin Polymerisation. Can. J. of Chem. Eng. Jun. 2012;90:646-71.
Church et al., Carbonylation of heterocycles by homogeneous catalysts. Chem. Commun. 2007;7:657-74. Epub Jan. 19, 2007.
Coasne et al., Temperature Effect on Adsorption/Desorption Isotherms for a Simple Fluid Confined within Various Nanopores. Adsorption. Jul. 2005; 11:289-94.
Colombo et al., High thermal and chemical stability in pyrazolate-bridged metal—organic frameworks with exposed metal sites. Chem. Sci. 2011;2:1311-9. Epub Apr. 28, 2011.
Comito et al., Single-Site Heterogeneous Catalysts for Olefin Polymerization Enabled by Cation Exchange in a Metal-Organic Framework. J. Am. Chem. Soc. 2016; 138(32):10232-7. Epub Jul. 21, 2016. Supporting Information Included.

(56) References Cited

OTHER PUBLICATIONS

Corma et al., Engineering Metal Organic Frameworks for Heterogeneous Catalysis. Chem. Rev. 2010;110(8):4606-55. Epub Apr. 1, 2010.
Critoph, Evaluation of alternative refrigerant—adsorbent pairs for refrigeration cycles. Applied Thermal Engineering. Nov. 1996;16(11):891-900.
Cui et al., An electroactive porous network from covalent metal—dithiolene links. Chem Commun. 2014;50:3986-8. Epub Feb. 24, 2014.
Cychosz et al., Water stability of microporous coordination polymers and the adsorption of pharmaceuticals from water. Langmuir. Nov. 16, 2010;26(22):17198-202. doi: 10.1021/la103234u. Epub Oct. 5, 2010.
De Lange et al., Adsorption-Driven Heat Pumps: The Potential of Metal—Organic Frameworks. Chem. Rev. 2015;115(22):12205-50. Epub Oct. 23, 2015.
De Lange et al., Metal—Organic Frameworks in Adsorption-Driven Heat Pumps: The Potential of Alcohols as Working Fluids. Langmuir. 2015;31(46):12783-96. Epub Nov. 2, 2015.
Denysenko et al., Elucidating Gating Effects for Hydrogen Sorption in MFU-4-Type Triazolate-Based Metal—Organic Frameworks Featuring Different Pore Sizes. Chem. Eur. J. 2011;17(6):1837-48. Epub Jan. 12, 2011.
Denysenko et al., Postsynthetic Metal and Ligand Exchange in MFU-41: A Screening Approach toward Functional Metal—Organic Frameworks Comprising Single-Site Active Centers. Chem. Eur. J. May 26, 2015;21(22):8188-99.
Denysenko et al., Reversible gas-phase redox processes catalyzed by Co-exchanged MFU-41(arge). Chem. Commun. 2012;48:1236-8. Epub Dec. 6, 2011.
Denysenko et al., Scorpionate-Type Coordination in MFU-41 Metal—Organic Frameworks: Small-Molecule Binding and Activation upon the Thermally Activated Formation of Open Metal Sites. Angew. Chemie Int. Ed. Jun. 2, 2014;53(23):5832-6.
Deria et al., Beyond post-synthesis modification: evolution of metal—organic frameworks via building block replacement. Chem. Soc. Rev. 2014;43:5896-912. Epub Apr. 11, 2014.
Desantis et al., Techno-economic Analysis of Metal—Organic Frameworks for Hydrogen and Natural Gas Storage. Energy Fuels. 2017;31(2):2024-32. Epub Jan. 4, 2017.
Dinca et al., DALTON Lecture: New Application of Metal-Organic Frameworks. UC Berkeley. Mar. 11, 2016. 49 pages.
Dinca et al., Designer Porous material for Clean Energy and Water. International Workshop on Advanced Materials. Al Hamra Fort, Ras al Khaimah, UAE. Feb. 2017. 7 pages.
Dinca et al., Teaching Sponges New Tricks: Redox Reactivity and Charge Transport in Microporous Metal-Organic Frameworks. Princeton University. Frick Chemistry Laboratory, Taylor Auditorium. Princeton, NJ. Sep. 14, 2015. 48 pages.
Dinca, Dynamic MOF SBUs as Active Sites for Small Molecule Reactivity and Catalysis. 253rd National ACS Meeting. San Francisco, CA. Apr. 2017. 10 pages.
Dinca, Teaching Sponges New Tricks: Small Molecule Chemistry and Charge Transport in Microporous Metal-Organic Frameworks. NSF Center for Chemical Innovation. Brown University. Providence, RI. May 2014. 4 pages.
Domski et al., Living alkene polymerization: New methods for the precision synthesis of polyolefins. Progress in Polymer Science. Jan. 2007;32(1):30-92.
Doonan et al., Exceptional ammonia uptake by a covalent organic framework. Nature Chemistry. 2010;2:235-8. Epub Feb. 7, 2010.
Ehrenmann et al., Water adsorption characteristics on MIL-101 for heat-transformation application of MOFs. Eur J Inorg Chem. 2011;2011(4):471-474.
Farrusseng et al., Metal—Organic Frameworks: Opportunities for Catalysis. Angew. Chemie Int. Ed. Sep. 28, 2009;48(41):7502-13.
Feigl et al., Über Verbindungen des Nickels mito-Phenylendiamin und 1, 3, 4-Toluylendiamin. Monatsh. Chem. Jul. 1927;48(7):445-50.

Férey et al., A Chromium Terephthalate-Based Solid with Unusually Large Pore Volumes and Surface Area. Science. Sep. 23, 2005;309(5743):2040-2.
Finiels et al., Nickel-based solid catalysts for ethylene oligomerization—a review. Catal. Sci. Technol. 2014;4:2412-26. Epub Apr. 16, 2014.
Froehlich et al., Multicycle water vapour stability of microporous breathing MOF aluminium isophthalate CAU-10-H. Dalton Trans. 2014;43:15300-4. Epub Aug. 26, 2014.
Furlan et al., Highly active zirconium(IV) catalyst containing sterically hindered hydridotris(pyrazolyl)borate ligand for the polymerization of ethylene. Macromolecular Rapid Communications. Oct. 2000;21(15):1054-7.
Furukawa et al., The chemistry and applications of metal-organic frameworks. Science. Aug. 30, 2013;341(6149):1230444. doi: 10.1126/science.1230444. 12 pages.
Furukawa et al., Water adsorption in porous metal-organic frameworks and related materials. J Am Chem Soc. Mar. 19, 2014;136(11):4369-81. doi: 10.1021/ja500330a. Epub Mar. 11, 2014.
Gandara et al., Porous, Conductive Metal-Triazolates and Their Structural Elucidation by the Charge-Flipping Method. Chem Eur J. Aug. 20, 2012; 18(34):10595-601. Epub Jun. 22, 2012.
Garcia-Orozco et al., Tris(pyrazolyl)methane-chromium(III) complexes as highly active catalysts for ethylene polymerization. Journal of Molecular Catalysis A: Chemical. Dec. 2006;260(1-2):70-6.
Gargiulo et al., Synthesis and characterization of a microporous copper triazolate as a water vapor adsorbent. Microporous and Mesoporous Mater. 2011;145:74-9.
Garzón-Tovar et al., Optimised room temperature, water-based synthesis of CPO-27-M metal—organic frameworks with high space-time yields. J. Mater. Chem. A. 2015;3:20819-26. Epub Sep. 9, 2015.
Getzler et al., Synthesis of β-Lactones: A Highly Active and Selective Catalyst for Epoxide Carbonylation. J. Am. Chem. Soc. 2002;124(7):1174-5. Epub Jan. 24, 2002.
Gil et al., Copolymerization of Ethylene with 1-Hexene Using Sterically Hindered Tris(pyrazolyl)borate Titanium (IV) Compounds. Macromolecular Chemistry and Physics. Jan. 2001;202(2):319-24.
Golubovic et al., Sorption properties for different types of molecular sieve and their influence on optimum dehumidification performance of desiccant wheels. Int. J. Heat Mass Transf. Aug. 2006;49(17-18):2802-9.
Guo et al., Adsorption of NH3 onto activated carbon prepared from palm shells impregnated with H2SO4. Journal of Colloid and Interface Science. Jan. 15, 2005;281(2):285-90.
Gutzler et al., π-Electron Conjugation in Two Dimensions. J Am Chem Soc. 2013; 135(44):16585-94. Epub Sep. 19, 2013.
Hao et al., Structurally Designed Synthesis of Mechanically Stable Poly(benzoxazine-co-resol)-Based Porous Carbon Monoliths and Their Application as High-Performance CO2 Capture Sorbents. J Am Chem Soc. 2011;133(29):11378-88. Epub Jun. 21, 2011.
Henninger et al., Characterisation and improvement of sorption materials with molecular modeling for the use of heat transformation applications. Adsorption. 2011;17:833-43.
Henninger et al., MOFs as adsorbents for low temperature heating and cooling applications. J Am Chem Soc. Mar. 4, 2009;131(8):2776-7. doi: 10.1021/ja808444z.
Henninger et al., MOFs for Use in Adsorption Heat Pump Processes. European Journal of Inorganic Chemistry. Jun. 2012; 2012(16):2625-34.
Henninger et al., Novel sorption materials for solar heating and cooling. Energy Procedia. 2012;30:279-88.
Henninger et al., Water adsorption characteristics of novel materials for heat transformation applications. Appl. Therm. Eng. 2010;30:1692-1702.
Herebian et al., Molecular and electronic structures of bis-(o-diiminobenzosemiquinonato)metal(II) complexes (Ni, Pd, Pt), their monocations and -anions, and of dimeric dications containing weak metal-metal bonds. J Am Chem Soc. Jul. 30, 2003;125(30):9116-28.
Hermes et al., Selective Nucleation and Growth of Metal-Organic Open Framework Thin Films on Patterned COOH/CF3-Terminated Self-Assembled Monolayers on Au(111). JACS. 2005;127:13744-5.

(56) References Cited

OTHER PUBLICATIONS

Hlatky, Heterogeneous Single-Site Catalysts for Olefin Polymerization. Chem. Rev. 2000;100:1347-76.

Hmadeh et al., New Porous Crystals of Extended Metal-Catecholates. Chemistry of Materials. 2012;24(18):3511-3. Epub Aug. 28, 2012.

House et al., The synthesis and X-ray structure of trans-[CrCl2(nPrNH2)4]BF4•H2O and the thermal and Hg2+-assisted chloride release kinetics from some trans-[CrCl2(N)4]+ complexes. Inorganica Chimica Acta. Sep. 1995;237(1-2):37-46.

Janchen et al., Studies of the water adsorption on Zeolites and modified mesoporous materials for seasonal storage of solar heat. Solar Energy. 2004;76:339-44.

Jasuja et al., Adjusting the Stability of Metal—Organic Frameworks under Humid Conditions by Ligand Functionalization. Langmuir. 2012;28(49):16874-80. Epub Nov. 7, 2012.

Jeon et al., Accelerated Life-time Tests including Different Load Cycling Protocols for High Temperature Polymer Electrolyte Membrane Fuel Cells. Electrochimica Acta. Dec. 1, 2014;148:15-25.

Jeremias et al., MIL-100(Al, Fe) as water adsorbents for heat transformation purposes—a promising application. J Mater Chem. 2012;22:10148-10151.

Jeremias et al., Programming MOFs for water sorption: amino-functionalized MIL-125 and UiO-66 for heat transformation and heat storage applications. Dalton Trans. Dec. 7, 2013;42(45):15967-73. doi: 10.1039/c3dt51471d. Epub Jul. 18, 2013.

Jeremias et al., Water and methanol adsorption on MOFs for cycling heat transformation processes. New J Chem. 2014;38:1846-52.

Kambe et al., Redox Control and High Conductivity of Nickel Bis(dithiolene) Complex π-Nanosheet: A Potential Organic Two-Dimensional Topological Insulator. J Am Chem Soc. 2014;136(41):14357-60. Epub Sep. 24, 2014.

Kambe et al., π-Conjugated Nickel Bis(dithiolene) Complex Nanosheet. J Am Chem Soc. 2013;135(7):2462-5. Epub Jan. 29, 2013.

Kaminsky et al., High melting polypropenes by silica-supported zirconocene catalysts. Makromol. Chem. Rapid. Commun. 1993;14:239-43.

Katz et al., High volumetric uptake of ammonia using Cu-MOF-74/Cu-CPO-27 . Dalton Trans. 2016;45:4150-3. Epub Sep. 24, 2015.

Khutia et al., Water sorption cycle measurements on functionalized MIL-101 Cr for heat transformation application. Chem Mater. 2013;25:790-798.

Killian et al., Preparation of Linear α-Olefins Using Cationic Nickel(II) α-Diimine Catalysts. Organometallic s. 1997;16(10):2005-7. Epub May 13, 1997.

Klet et al., Single-Site Organozirconium Catalyst Embedded in a Metal—Organic Framework. J. Am. Chem. Soc. 2015;137(50):15680-83. Epub Dec. 14, 2015.

Kobayashi et al., Conductivity, Doping, and Redox Chemistry of a Microporous Dithiolene-Based Metal—Organic Framework. Chem Mater. 2010;22(14):4120-2. Epub Jun. 25, 2010.

Kong et al., Opportunities in chemistry and materials science for topological insulators and their nanostructures. Nature Chemistry. 2011;3:845-9. Epub Oct. 24, 2011.

Kramer et al., Practical β-Lactone Synthesis: Epoxide Carbonylation at 1 atm. Org. Lett. 2006;8(17):3709-12. Epub Jul. 18, 2006.

Kreno et al., Metal—Organic Framework Materials as Chemical Sensors. Chemical Reviews. 2012;112(2):1105-25. Epub Nov. 9, 2011.

Kunrath et al., Highly Selective Nickel Ethylene Oligomerization Catalysts Based on Sterically Hindered Tris(pyrazolyl)borate Ligands. Organometallics. 2003;22:4739-43. Epub Oct. 9, 2003.

Kusgens et al., Characterization of metal-organic frameworks by water adsorption. Microporous and Mesoporous Mater. 2009;120:325-330.

Lallemand et al., Catalytic oligomerization of ethylene over Ni-containing dealuminated Y zeolites. Appl. Catal. A Gen. Feb. 2006;301:196-201.

Lallemand et al., Ethylene oligomerization over Ni-containing mesostructured catalysts with MCM-41, MCM-48 and SBA-15 topologies. Studies in Surface Science and Catalysis. 2007;170:1863-9. Epub Oct. 18, 2007.

Lallemand et al., Ni-MCM-36 and Ni-MCM-22 catalysts for the ethylene oligomerization. Studies in Surface Science and Catalysis. 2008;174:1139-42. Epub Nov. 6, 2008.

Li et al., Design and synthesis of an exceptionally stable and highly porous metal-organic framework. Nature. 1999;402:276-9. Epub Nov. 18, 1999.

Li et al., Highly active self-immobilized FI-Zr catalysts in a PCP framework for ethylene polymerization. Chem. Commun. 2015;51:16703-6. Epub Sep. 21, 2015.

Li et al., Reductive electrosynthesis of Crystalline Metal-Organic frameworks. JACS. 2011;133:12926-9.

Liao et al., Drastic Enhancement of Catalytic Activity via Post-oxidation of a Porous MnII Triazolate Framework. Chem. Eur. J. Sep. 1, 2014;20(36):11303-7.

Liu et al., High-Performance Chemical Sensing Using Schottky-Contacted Chemical Vapor Deposition Grown Monolayer MoS2 Transistors. ACS Nano. 2014;8(5):5304-14. Epub Apr. 21, 2014.

Liu et al., Postsynthetic modification of mixed-linker metal-organic frameworks for ethylene oligomerization. RSC Adv. 2014;4:62343-6. Epub Nov. 13, 2014.

Liu et al., Single-Walled Carbon Nanotube—Metalloporphyrin Chemiresistive Gas Sensor Arrays for Volatile Organic Compounds. Chern. Mater. 2015;27(10):3560-3. Epub May 8, 2015.

Low et al., Virtual high throughput screening confirmed experimentally: porous coordination polymer hydration. J. Am. Chem. Soc. Nov. 4, 2009;131(43):15834-42. doi: 10.1021/ja9061344.

Luna et al., Evaluation of Commercial Off-the-Shelf Sorbents and Catalysts for Control of Ammonia and Carbon Monoxide. American Institute of Aeronautics and Astronautics. 2008. 15 pages.

Ma et al., A series of isoreticular chiral metal—organic frameworks as a tunable platform for asymmetric catalysis. Nat. Chem. 2010;2:838-46. Epub Jul. 25, 2010.

Mahadevan et al., [Lewis Acid]+[Co(CO)4]—Complexes: A Versatile Class of Catalysts for Carbonylative Ring Expansion of Epoxides and Aziridines. Angew. Chem. Int. Ed. 2002;41(15):2781-4.

Makal et al., Methane storage in advanced porous materials. Chem Soc Rev. Dec. 7, 2012;41(23):7761-79. doi: 10.1039/c2cs35251f.

Maki et al., Electron Paramagnetic Resonance Studies of the Electronic Structures of Bis(maleonitriledithiolato)copper(II), -nickel(III), -cobalt(II), and -rhodium(II) Complexes. J. Am Chem. Soc. Nov. 1964;86(21):4580-7.

Marshall et al., Single-Crystal to Single-Crystal Mechanical Contraction of Metal-Organic Frameworks through Stereoselective Postsynthetic Bromination. J. Am. Chem. Soc. 2015;137:9527-30. Epub Jul. 15, 2015.

Merica et al., Synthesis of nitropolychlorinated dibenzo-p-dioxins (NPCDDs) and their photochemical reaction with nucleophiles. Can. J. Chem. 1995;73:826-35.

Metzger et al., Selective Dimerization of Ethylene to 1-Butene with a Porous Catalyst. ACS Cent. Sci. 2016;2(3):148-53. Epub Feb. 19, 2016. Supporting Information Included.

Miner et al., Electrochemical oxygen reduction catalysed by Ni3(hexaiminotriphenylene)2. Nat Commun. Mar. 2016;7:10942. 7 pages.

Mlinar et al., Selective Propene Oligomerization with Nickel(II)-Based Metal—Organic Frameworks. ACS Catal. 2014;4(3):717-21. Epub Jan. 27, 2014.

Mondloch et al., Destruction of chemical warfare agents using metal—organic frameworks. Nat. Mater. 2015;14:512-6. Epub Mar. 16, 2015.

Murtuza et al., Ethylene Polymerization Behavior of Tris(pyrazolyl)borate Titanium(IV) Complexes. Organometallics. 2002;21(9): 1882-90. Epub Mar. 28, 2002.

Narayan et al., High Charge Mobility in a Tetrathiafulvalene-Based Microporous Metal—Organic Framework. J Am Chem Soc. 2012;134(31):12932-5. Epub Jul. 24, 2012.

(56) References Cited

OTHER PUBLICATIONS

Narayanan et al., Optimization of adsorption processes for climate control and thermal energy storage. Int. J. Heat Mass Transf. Oct. 2014;77:288-300.
Ng et al., Experimental investigation of the silica gel-water adsorption isotherm characteristics. Appl. Therm Eng. 2001;21:1631-42.
Nguyen et al., High Methanol Uptake Capacity in Two New Series of Metal—Organic Frameworks: Promising Materials for Adsorption-Driven Heat Pump Applications. Chem. Mater. 2016;28(17):6243-9. Epub Aug. 8, 2016.
Noro et al., Metal-organic thin-film transistor (MOTFT) based on a bis(o-diiminobenzosemiquinonate) nickel(II) complex. J Am Chem Soc. Jul. 20, 2005;127(28):10012-3.
Park et al., Cation-Dependent Intrinsic Electrical Conductivity in Isostructural Tetrathiafulvalene-Based Microporous Metal—Organic Frameworks. J. Am. Chem. Soc. 2015;137(5):1774-7. Epub Jan. 18, 2015.
Park et al., Single-Ion Li+, Na+, and Mg2+ Solid Electrolytes Supported by a Mesoporous Anionic Cu-Azolate Metal—Organic Framework. J. Am. Chem. Soc. 2017;139(38):13260-3. Epbu Sep. 7, 2017.
Petit et al., The role of sulfur-containing groups in ammonia retention on activated carbons. Carbon. Mar. 2010;48(3):654-67.
Petit et al., Toward Understanding Reactive Adsorption of Ammonia on Cu-MOF/Graphite Oxide Nanocomposites. Langmuir. 2011;27(21):13043-51. Epub Oct. 4, 2011.
Pommier et al., Recent Advances in β-Lactone Chemistry. Synthesis. 1993;5:441-59.
Qajar et al., Enhanced ammonia adsorption on functionalized nanoporous carbons. Microporous and Mesoporous Materials. Dec. 1, 2015;218:15-23.
Rieth et al., High and Reversible Ammonia Uptake in Mesoporous Azolate Metal—Organic Frameworks with Open Mn, Co, and Ni Sites. J. Am. Chem. Soc. 2016;138(30):9401-4. Epub Jul. 15, 2016. Supporting Information Included.
Rieth et al., Record Atmospheric Fresh Water Capture and Heat Transfer with a Material Operating at the Water Uptake Reversibility Limit. ACS Cent. Sci. 2017;3(6):668-72. Epub May 24, 2017. Supporting Information Included.
Ristic et al., The performance of small-pore microporous aluminophosphates in low-temperature solar energy storage: the structure-property relationship. Adv Func Mater. 2012;22:1952-7.
Saha et al., Fundamental and application aspects of adsorption cooling and desalination. Appl. Therm. Eng. Mar. 25, 2016;97:68-76.
Schmidt et al., A Readily Synthesized and Highly Active Epoxide Carbonylation Catalyst Based on a Chromium Porphyrin Framework: Expanding the Range of Available β-Lactones. Org. Lett. 2004;6(3):373-6. Epub Jan. 8, 2008.
Schmidt et al., Chromium(III) Octaethylporphyrinato Tetracarbonylcobaltate: A Highly Active, Selective, and Versatile Catalyst for Epoxide Carbonylation. J. Am. Chem. Soc. 2005;127(32):11426-35. Epub Jul. 16, 2005.
Schoenecker et al., Effect of water adsorption on retention of structure and surface area of metal-organic frameworks. Ind Eng Chem Res. 2012;51:6513-6519.
Severn et al., "Bound but Not Gagged"Immobilizing Single-Site α-Olefin Polymerization Catalysts. Chem. Rev. 2005;105:4073-147. Epub Oct. 22, 2005.
Shamir, New synthesis of chromium trichloride tetrahydrofuranate. Inorganica Chimica Acta. Feb. 15, 1989;156(2):163-4.
Sheberla et al., Conductive MOF electrodes for stable supercapacitors with high areal capacitance. Nature Materials. 2017;16:220-4. Epub Oct. 10, 2016. Supporting Information Included.
Sheberla et al., High Electrical Conductivity in Ni3(2,3,6,7,10,11-hexaiminotriphenylene)2, a Semiconducting Metal—Organic Graphene Analogue. J Am Chem Soc. 2014;136(25):8859-62. Epub Apr. 21, 2014. Supporting Information Included.

Shustova et al., Selective Turn-On Ammonia Sensing Enabled by High-Temperature Fluorescence in Metal—Organic Frameworks with Open Metal Sites. J Am Chem Soc. 2013;135(36):13326-9. Epub Aug. 27, 2013.
Speiser et al., Catalytic Ethylene Dimerization and Oligomerization: Recent Developments with Nickel Complexes Containing P,N-Chelating Ligands. Acc. Chem. Res. 2005;38(10):784-93. Epub Sep. 9, 2005.
Stavila et al., MOF-based electronic and opto-electronic devices. Chem Soc Rev. Aug. 21, 2014;43(16):5994-6010. doi: 10.1039/c4cs00096j.
Stiefel et al., The Myth of Nickel(III) and Nickel(IV) in Planar Complexes. J. Am. Chem. Soc. Jul. 1965;87(13):3016-7.
Stoeckli et al., Specific and non-specific interactions between ammonia and activated carbons. Carbon. 2004;42(8-9): 1619-24.
Suh et al., Hydrogen storage in metal-organic frameworks. Chem Rev. 2012;112:782-835.
Sumida et al., Carbon dioxide capture in metal-organic frameworks. Chem Rev. Feb. 8, 2012;112(2):724-81. doi: 10.1021/cr2003272. Epub Dec. 28, 2011.
Sun et al., Electrically Conductive Porous Metal-Organic Frameworks. Angew Chem Int Ed Engl. Mar. 7, 2016,55(11):3566-79. doi: 10.1002/anie.201506219. Epub Jan. 8, 2016. Review.
Sun et al., Measuring and Reporting Electrical Conductivity in Metal—Organic Frameworks: Cd2(TTFTB) as a Case Study. J Am Chem Soc. 2016; 138(44):14772-82. Epub Oct. 21, 2016.
Sun et al., Mn?(2,5-disulfhydrylbenzene-1,4-dicarboxylate): A Microporous Metal—Organic Framework with Infinite (-Mn—S-)∞ Chains and High Intrinsic Charge Mobility. J Am Chem Soc. 2013; 135(22):8185-8. Epub May 14, 2013.
Svejda et al., Ethylene Oligomerization and Propylene Dimerization Using Cationic (α-Diimine)nickel(II) Catalysts. Organometallics. 1999;18(1):65-74. Epub Dec. 15, 1998.
Talin et al., Tunable electrical conductivity in metal-organic framework thin-film devices. Science. Jan. 3, 2014;343(6166):66-9. doi: 10.1126/science.1246738. Epub Dec. 5, 2013.
Tamainot-Telto et al., Carbon—ammonia pairs for adsorption refrigeration applications: ice making, air conditioning and heat pumping. International Journal of Refrigeration. Sep. 2009;32(6):1212-29.
Tatsidjodoung et al., A review of potential materials for thermal energy storage in building applications. Renew. Sust. Energ. Rev. 2013;18:327-49.
Teufel et al., MFU-4—A Metal-Organic Framework for Highly Effective H2/D2 Separation. Adv. Mater. Jan. 2013;25(4):635-9.
Theopold, Homogeneous Chromium Catalysts for Olefin Polymerization. Eur J Inorg Chem. Jan. 1998;1:15-24.
Tonigold et al., Pyrazolate-based cobalt(II)-containing metal-organic frameworks in heterogeneous catalytic oxidation reactions: elucidating the role of entatic states for biomimetic oxidation processes. Chemistry. Jul. 25, 2011;17(31):8671-95. doi: 10.1002/chem.201003173. Epub Jun. 17, 2011.
Tulchinsky et al., Reversible Capture and Release of Cl2 and Br2 with a Redox-Active Metal—Organic Framework. J. Am. Chem. Soc. 2017;139(16):5992-7. Epub Mar. 28, 2017.
Van Humbeck et al., Ammonia Capture in Porous Organic Polymers Densely Functionalized with Brønsted Acid Groups. J. Am. Chem. Soc. 2014;136(6):2432-40. Epub Jan. 23, 2014.
Wade et al., Facile Deposition of Multicolored Electrochromic Metal—Organic Framework Thin Films. Angew Chem. Int. Ed. 2013;52(50):13377-81. Epub Oct. 16, 2013.
Wade et al., Investigation of the synthesis, activation, and isosteric heats of CO2 adsorption of the isostructural series of metal-organic frameworks M3(BTC)2 (M=Cr, Fe, Ni, Cu, Mo, Ru). Dalton Trans. Jul. 14, 2012;41(26):7931-8. doi: 10.1039/c2dt30372h. Epub Apr. 26, 2012.
Wade et al., Postsynthetic tuning of hydrophilicity in pyrazolate MOFs to modulate water adsorption properties. Energy Environ. Sci. 2013;6:2172-7.
Wade, Designing functionality for anion detection with molecular receptors and small molecule adsorption in microporous materials. PowerPoint Presentation. Brandeis University. Dec. 4, 2012. 50 pages.

(56) References Cited

OTHER PUBLICATIONS

Wang et al., A review on adsorption working pairs for refrigeration. Renewable and Sustainable Energy Reviews. Apr. 2009;13(3):518-34.

Wang et al., Organic topological insulators in organometallic lattices. Nat Commun. 2013;4:1471. Epub Feb. 12, 2013. 5 pages.

Wang et al., Prediction of a Two-Dimensional Organic Topological Insulator. Nano Lett. 2013;13(6):2842-5. Epub May 16, 2013.

Wang et al., Pyrazolate-Based Porphyrinic Metal—Organic Framework with Extraordinary Base-Resistance. J. Am. Chem. Soc. 2016;138(3):914-9. Epub Dec. 30, 2015.

Wickenheisser et al., Grafting of hydrophilic ethylene glycols or ethylenediamine on coordinatively unsaturated metal sites in MIL-100(Cr) for improved water adsorption characteristics. Inorganica Chimica Acta. 2013;407:145-52.

Wu et al., A Homochiral Porous Metal—Organic Framework for Highly Enantioselective Heterogeneous Asymmetric Catalysis. J. Am. Chem. Soc. 2005;127(25):8940-1. Epub Jun. 4, 2005.

Wu et al., Adsorption sites and binding nature of CO2 in prototypical metal-organic frameworks: a combined neutron diffraction and first-principles study. J Phys Chem Lett. 2010;1(13):1946-51.

Xiao et al., Oxidation of ethane to ethanol by N2O in a metal-organic framework with coordinatively unsaturated iron(II) sites. Nat Chem. Jul. 2014;6(7):590-5. doi: 10.1038/nchem.1956. Epub May 18, 2014.

Yamada et al., First-Principles Design of Half-Filled Flat Band of the Kagome Lattice in Two-Dimensinoal Metal-Organic Frameworks. Jul. 26, 2016. arXiv:1510.00164v3.

Yamazoe et al., Receptor Function and Response of Semiconductor Gas Sensor. Journal of Sensors. 2009;2009:21 pages.

Yang et al., Temperature-Triggered Collection and Release of Water from Fogs by a Sponge-Like Cotton Fabric. Adv. Mater. Feb. 25, 2013;25(8):1150-4.

Zhang et al., Ethylene Oligomerization Over Heterogeneous Catalysts. Energy and Environment Focus. Sep. 2014;3(3):246-56.

Partial European Search Report for EP 17803667 dated Jan. 2, 2020.

Extended European Search Report for EP 17803667 dated Apr. 2, 2020.

Park et al., Heterogeneous Epoxide Carbonylation by Cooperative Ion-Pair Catalysis in Co(CO)4—Incorporated Cr-MIL-101. ACS Cent. Sci. 2017;3(5):444-8. Epub Mar. 21, 2017. Supporting Information Included.

\* cited by examiner

COMPOSITIONS AND METHODS FOR SELECTIVE CARBONYLATION OF HETEROCYCLIC COMPOUNDS

RELATED APPLICATIONS

The present application is a national stage filing under 35 U.S.C. 371 of International Patent Application Serial No. PCT/US2017/055035, filed Oct. 4, 2017, entitled "Compositions and Methods for Selective Carbonylation of Heterocyclic Compounds," which claims priority under 35 U.S.C. § 119(e) to U.S. provisional application, U.S. Ser. No. 62/403,938, filed Oct. 4, 2016, entitled "Compositions Comprising Metal Organic Frameworks and Related Methods and Uses Including Heterogeneous Catalysis," each of which is incorporated herein by reference in its entirety for all purposes.

FIELD OF INVENTION

Described herein are compositions comprising metal organic frameworks and related methods and uses, including use in selective carbonylation of heterocyclic compounds.

BACKGROUND

Heterogeneous catalysts provide a variety of benefits as compared to homogenous catalysts. For example, heterogeneous catalyst are more readily separated from the reaction mixture (e.g., filtration). For many beneficial chemical products, no heterogeneous catalysts are currently available to aid in their synthesis. For example, β-lactones are one key intermediate in numerous synthetic pathways. Such versatility stems from the inherent ring strain in the four-membered β-lactones, which renders them highly susceptible to a rich variety of ring-opening and ring-expanding transformations. The high commercial value of the resulting products, including β-hydroxycarbonyls, biodegradable poly(hydroxyalkanoate)s, and succinic anhydrides, illustrates the industrial relevance of β-lactone chemistry. Yet one bottleneck that has hampered the wide use of β-lactones has been their challenging synthesis. Ring expansion carbonylation of epoxides has been developed as a viable route to β-lactones. However, known epoxide carbonylation processes generally rely on homogeneous catalyst systems, which significantly increase separation costs, hindering widespread use.

Due to the homogeneous nature of the employed catalysts in known processes, the processes require a product/catalyst recovery step that involves thermal volatilization of the β-lactones from the product mixture. This step often requires a concurrent reduction in pressure to decrease the boiling point of the β-lactones, which is presumably needed to minimize the thermal degradation of the unstable β-lactones. This simultaneous heat/pressure modification is extremely energy-intensive and thus expensive, but is required in a process that uses homogeneous catalysts.

Accordingly, improved catalysts and methods for the formation of organic products, including but not limited to β-lactones and secondary products formed from β-lactones and other substrates, are needed.

SUMMARY OF THE INVENTION

Described herein are compositions comprising metal organic frameworks and related methods and uses.

In some embodiments, a composition is provided. The composition may comprise a metal organic framework compound comprising a plurality of metal ions, each coordinated with at least one ligand. The composition may further comprise a plurality of $Co(CO)_4^-$ anions associated with at least a portion of the metal ions.

In some embodiments, a method of synthesizing a composition is provided. The method may comprise exposing a metal organic framework (MOF) comprising a plurality of metal ions, each coordinated with at least one ligand, to a solution comprising a plurality of $Co(CO)_4^-$ anions, thereby forming a composition comprising the MOF having at least a portion of the metal ions associated with a $Co(CO)_4^-$ anion.

In some embodiments, a method is provided. The method may comprise exposing carbon monoxide and an epoxide substrate having the formula,

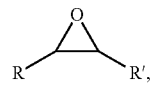

to the above composition or a composition made by the above method, thereby forming a β-lactone having the formula,

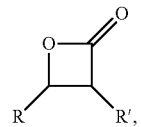

wherein R and R' may be the same or different and are hydrogen, an optionally substituted aliphatic group, an optionally substituted heteroaliphatic group, or an optionally substituted aromatic groups, or alternatively, R and R' may join to form an optionally substituted alicyclic compound.

In some embodiments, a method is provided. The method may comprise exposing carbon monoxide and an epoxide substrate having the formula,

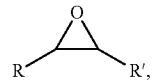

to a heterogeneous catalyst thereby forming a β-lactone having the formula,

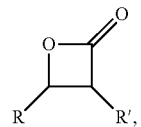

wherein R and R' may be the same or different and are hydrogen, an optionally substituted aliphatic group, an optionally substituted heteroaliphatic group, or an optionally substituted aromatic groups, or alternatively, R and R' may join to form an optionally substituted alicyclic compound, wherein the β-lactone is formed with a selectivity of at least about 50%. The method may further comprise forming a product having the formula,

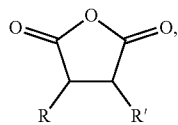

from the β-lactone having the formula,

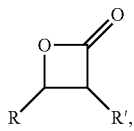

upon further exposure to the composition or heterogeneous catalyst, wherein the product is formed with a selectivity of at least about 50%.

In some embodiments, a method is provided. The method may comprise exposing carbon monoxide and a β-lactone having the formula,

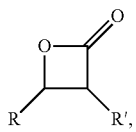

to a composition of any preceding claim or a composition made by a method of any preceding claim, thereby forming a product having the formula,

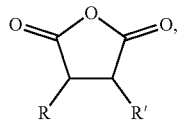

wherein R, R' and R" may be the same or different and are hydrogen, an optionally substituted aliphatic group, an optionally substituted heteroaliphatic group, or an optionally substituted aromatic groups, or alternatively, R and R' may join to form an optionally substituted alicyclic compound, and wherein the product is formed with a selectivity of at least about 50%.

In some embodiments a method is provided. The method may comprise exposing carbon monoxide and a substrate having the formula,

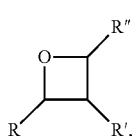

to a heterogeneous catalyst thereby forming a product having the formula,

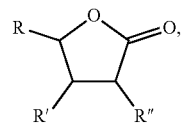

wherein R, R' and R" may be the same or different and are hydrogen, an optionally substituted aliphatic group, an optionally substituted heteroaliphatic group, or an optionally substituted aromatic groups, or alternatively, R and R' may join to form an optionally substituted alicyclic compound, and wherein the product is formed with a selectivity of at least about 50%.

In some embodiments a method is provided. The method may comprise exposing carbon monoxide and a substrate having the formula, exposing carbon monoxide and a substrate having the formula,

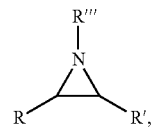

to a heterogeneous catalyst thereby forming a product having the formula,

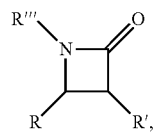

wherein R and R' are the same or different and are hydrogen, an optionally substituted aliphatic group, an optionally substituted heteroaliphatic group, or an optionally substituted aromatic groups, or R and R' joins to form an optionally substituted alicyclic compound, wherein R''' is hydrogen, an optionally substituted aliphatic group, an optionally substituted heteroaliphatic group, an optionally substituted aromatic groups, or a nitrogen protecting group, and wherein the product is formed with a selectivity of at least about 50%.

In some embodiments a method is provided. The method may comprise exposing carbon monoxide and a substrate having the formula,

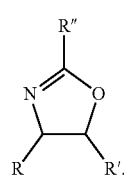

to a heterogeneous catalyst thereby forming a product having the formula,

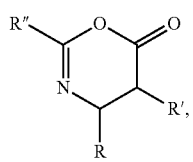

wherein R, R' and R" may be the same or different and are hydrogen, an optionally substituted aliphatic group, an optionally substituted heteroaliphatic group, or an optionally substituted aromatic groups, or alternatively, R and R' may join to form an optionally substituted alicyclic compound, and wherein the product is formed with a selectivity of at least about 50%.

Other advantages and novel features of the present invention will become apparent from the following detailed description of various non-limiting embodiments of the invention when considered in conjunction with the accompanying figures. Unless otherwise noted, all references cited herein are incorporated by reference in their entirety. In cases where the present specification and a document incorporated by reference include conflicting and/or inconsistent disclosure, the present specification shall control.

BRIEF DESCRIPTION OF THE DRAWINGS

Non-limiting embodiments of the present invention will be described by way of example with reference to the accompanying figures, which are schematic and are not intended to be drawn to scale. In the figures, each identical or nearly identical component illustrated is typically represented by a single numeral. For purposes of clarity, not every component is labeled in every figure, nor is every component of each embodiment of the invention shown where illustration is not necessary to allow those of ordinary skill in the art to understand the invention. In the figures.

DETAILED DESCRIPTION

Figure 1:
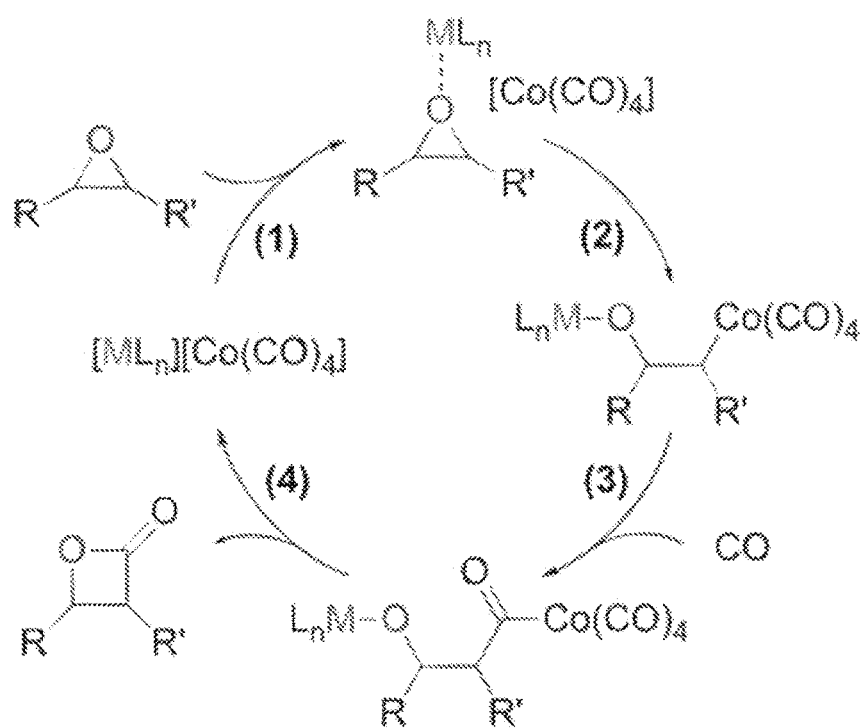
FIG. 1 shows a proposed catalytic cycle for the ring-expansion carbonylation of epoxides, according to one or more non-limiting embodiments.

Compositions comprising metal organic frameworks (MOFs) and related methods and uses are generally provided, including use in heterogeneous catalysis. In some embodiments, the compositions generally comprise an MOF and a plurality of $Co(CO)_4^-$ anions. In some embodiments, the compositions may be used as heterogeneous catalysts for carbonylation reactions (e.g., the carbonylation of epoxides and β-lactones).

In some embodiments, the disclosed compositions may be employed in catalytic carbonylation reactions (e.g., for the ring-expansion carbonylation of epoxides and β-lactones). In some embodiments, the activity and/or selectivity is high. In some embodiments, the use of a heterogeneous catalyst may circumvent the product/catalyst recovery step generally required in homogeneous catalyst systems, as the heterogeneous catalyst can be physically separated from the product via, for example, a packed-bed reactor setup or a downstream filtration. This can reduce the operating cost of the process, giving it a competitive advantage over a process that relies on homogeneous catalysts. In this regard, the MOF-based heterogeneous catalyst disclosed herein is an ideal candidate for use in an epoxide or β-lactone carbonylation process, as it exhibits catalytic activity comparable to that of the homogeneous catalysts and also allows the innate advantages of heterogeneous catalysis. In some embodiments, the heterogeneous nature of the MOF-based catalysts allows these catalysts to be used in any type of reactor suitable for catalytic carbonylation reaction (e.g., carbonylation of epoxides and β-lactones).

It should be understood, that while much of the following description relates to the carbonylation of epoxides and β-lactones, this is by no means limiting, and the methods, compositions, and systems described herein may be used for other carbonylation reactions, as described in more detail herein.

In some applications, the disclosed methods and compounds may replace known homogeneous catalysts in a batch-wise process for carbonylation reactions (e.g., epoxide or β-lactone carbonylation). The disclosed heterogeneous catalysts may be introduced to a batch reactor along with a substrate (e.g., epoxide or β-lactone), solvent, and CO. After the reaction, the catalyst may be recovered from the product mixture through filtration or other separation techniques and the recovered catalyst may be reused in subsequent reaction cycles.

In other applications, the disclosed heterogeneous catalysts may be used in continuous processes for catalytic carbonylation reactions. The catalyst may be immobilized in a packed-bed reactor while a substrate, solvent, and CO are passed through the packed-bed. The same setup can be used with neat or gas-phase substrates, and with recycle loops as well.

In some embodiments, the heterogeneous catalyst comprises a metal organic framework (MOF) comprising a plurality of metal ions and a plurality of $Co(CO)_4^-$ anions associated with at least a portion of the metal ions. In some embodiments, the heterogeneous catalyst may be formed by exposing a metal organic framework (MOF) comprising a plurality of metal ions, each coordinated with at least one ligand, to a solution comprising a plurality of $Co(CO)_4^-$ anions, thereby forming a composition comprising the MOF having at least a portion of the metal ions associated with a $Co(CO)_4^-$ anion. Additional details regarding the MOFs and methods for forming the compositions comprising an MOF are described herein.

In some embodiments, the composition is a heterogeneous catalyst. The term "heterogeneous catalyst" is given its ordinary meaning in the art and generally refers to a catalyst that is of a different phase than the reactants. In some embodiments, the heterogeneous catalyst is in the solid phase and the reactants are in the gaseous phase. In some embodiments the heterogeneous catalyst is in the solid phase and the reactants are in the liquid phase. In some embodiments, the MOFs described herein are utilized in a solid state, for example, as a solid dispersed in a solution. One non-limiting advantage to heterogeneous catalysts is the catalyst may generally be easily separated from a reaction mixture.

Figure 2:
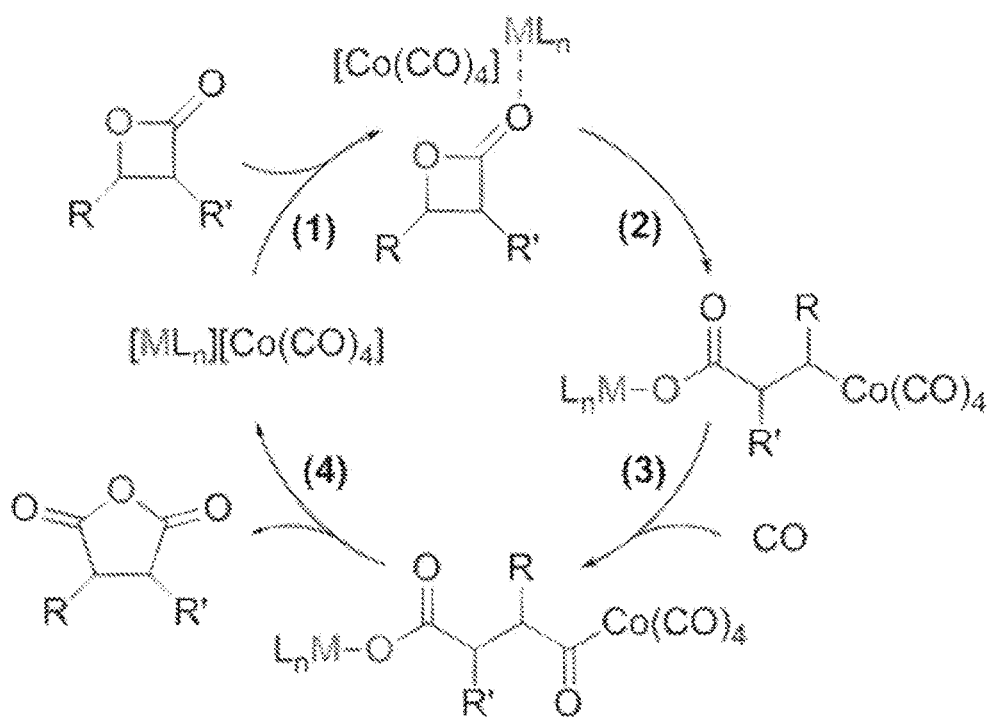
FIG. 2 shows a proposed catalytic cycle for the ring-expansion carbonylation of β-lactones, according to one or more non-limiting embodiments.

Without wishing to be bound by theory, the compositions described herein may function in a carbonylation reaction as follows. The metal ions at the nodes of the MOF may engage in a cooperative action with the Co(CO)$_4^-$ anions to activate the substrate (e.g., epoxide) and promote carbon monoxide insertion. FIG. 1 shows a non-limiting exemplary catalytic cycle, according to some embodiments, for the carbonylation of epoxides by [Lewis acid]$^+$[Co(CO)$_4$]$^-$ and FIG. 2 shows a non-limiting exemplary catalytic cycle, according to some embodiments, for the carbonylation of β-lactones by [Lewis acid]$^+$[Co(CO)$_4$]$^-$. The steps of the cycle shown in FIG. 1 and FIG. 2 may include: (1) substrate activation by [Lewis acid]$^+$, (2) attack by CO(CO)$_4^-$, (3) migratory insertion and uptake of CO, and (4) ring closing and extrusion. As shown in FIG. 1, the epoxide comprises Formula (I):

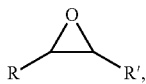
(I)

wherein R and R' may be the same or different and are hydrogen, an optionally substituted aliphatic group, an optionally substituted heteroaliphatic group, or an optionally substituted aromatic groups, or alternatively, R and R' may join to form an optionally substituted alicyclic compound.

According to some embodiments, CO and a substrate (e.g., epoxide or β-lactone) may be exposed to a composition described herein (e.g., comprising a MOF associated with a plurality of Co(CO)$_4^-$ anions) thereby forming a product (e.g., via carbonylation of the substrate), wherein the product is formed with a selectivity of at least about 50%, at least about 55%, at least about 60%, at least about 65%, at least about 70%, at least about 75%, at least about 80%, at least about 85%, at least about 90%, or at least about 95%. Those of ordinary skill in the art will be aware of methods for determining the selectivity of a reaction. The selectivity is given its ordinary meaning in the art and generally refers to the moles of that selected product divided by the total number of moles of all organic products (not including the substrate) recovered and multiplied by 100%. The moles of the selected product and all other organic products may be determined using methods known in the art (e.g., NMR, IR, etc.).

In certain embodiments, the MOF may catalyze the formation of a product with a high turnover. Turnover, as used herein, it given its ordinary meaning of the art and generally refers to the number of moles of product produced per moles of active metal centers in the MOF. In some embodiments, turnover is calculated with respect to the moles of cobalt present. In some embodiments, the product is produced at a turnover of at least about 20 moles, at least about 50 moles, at least about 80 moles, at least about 100 moles, at least about 150 moles, at least about 180 moles, or at least about 200 moles per hour per moles of active metal centers (e.g., Co(CO)$_4^-$ ions) at a pressure of about 60 bar of CO.

Figure 3:
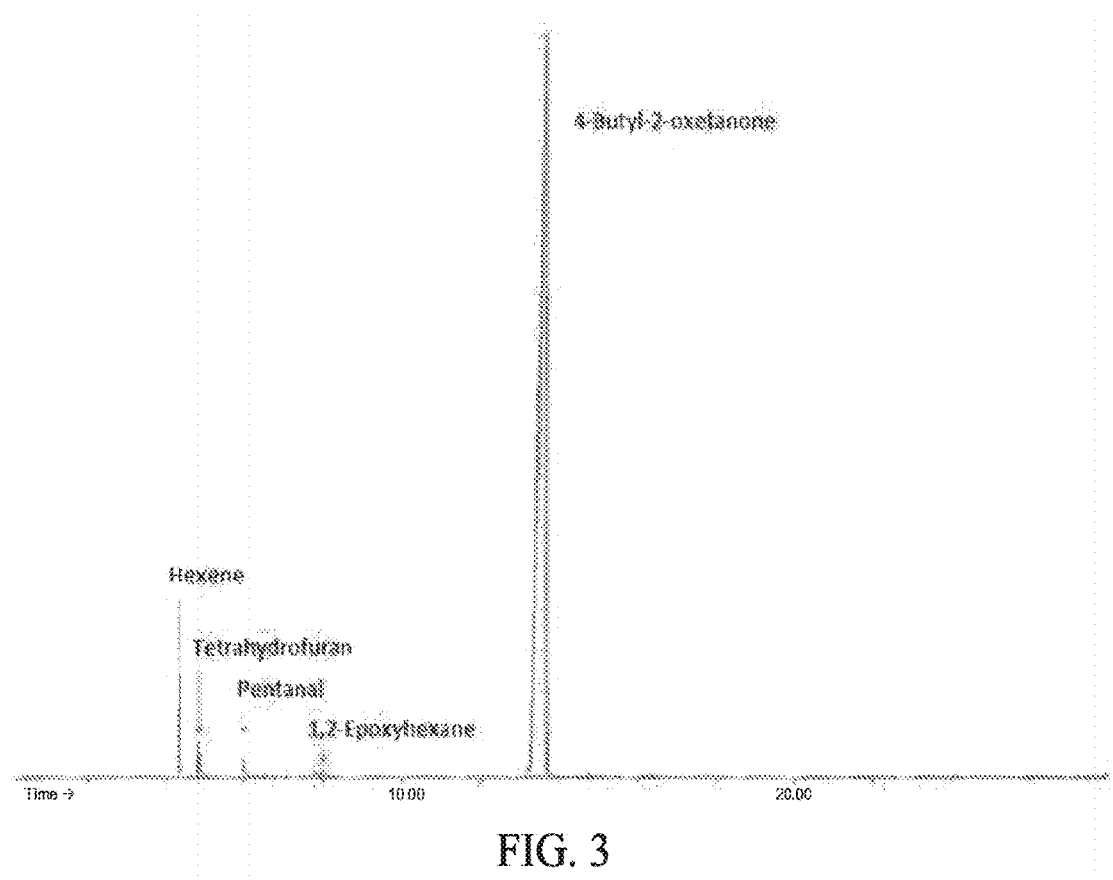
FIG. 3 shows a graphical representation of β-lactone formation from an epoxide, according to one or more non-limiting embodiments.

According to some embodiments, methods for the carbonylation of epoxides are generally provided. In some embodiments, the epoxide is carbonylated to form a β-lactone. The method may comprise exposing an epoxide and carbon monoxide to a composition as described herein (e.g., comprising an MOF and a plurality of Co(CO)$_4^-$ anions), thereby forming a β-lactone. In some embodiments, the epoxide comprises the structure shown in Formula (I), above, wherein R and R' may be the same or different and are hydrogen, an optionally substituted aliphatic group, an optionally substituted heteroaliphatic group, or an optionally substituted aromatic groups, or alternatively, R and R' may join to form an optionally substituted alicyclic compound. In some embodiments, the product formed via carbonylation of a Formula (I) species comprises a β-lactone, for example, comprising Formula (II):

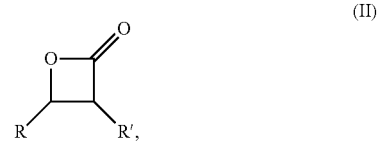
(II)

wherein R and R' are as described above in connection with Formula (I) (as shown in FIG. 3).

In some embodiments, the product of the initial carbonylation reaction (e.g., a β-lactone) may undergo further reaction to form additional products. In some embodiments, the product of the initial carbonylation reaction may undergo further catalytic reaction to form additional products. In some embodiments, the product of the initial carbonylation reaction (e.g., a β-lactone) may undergo further carbonylation.

Figure 4:
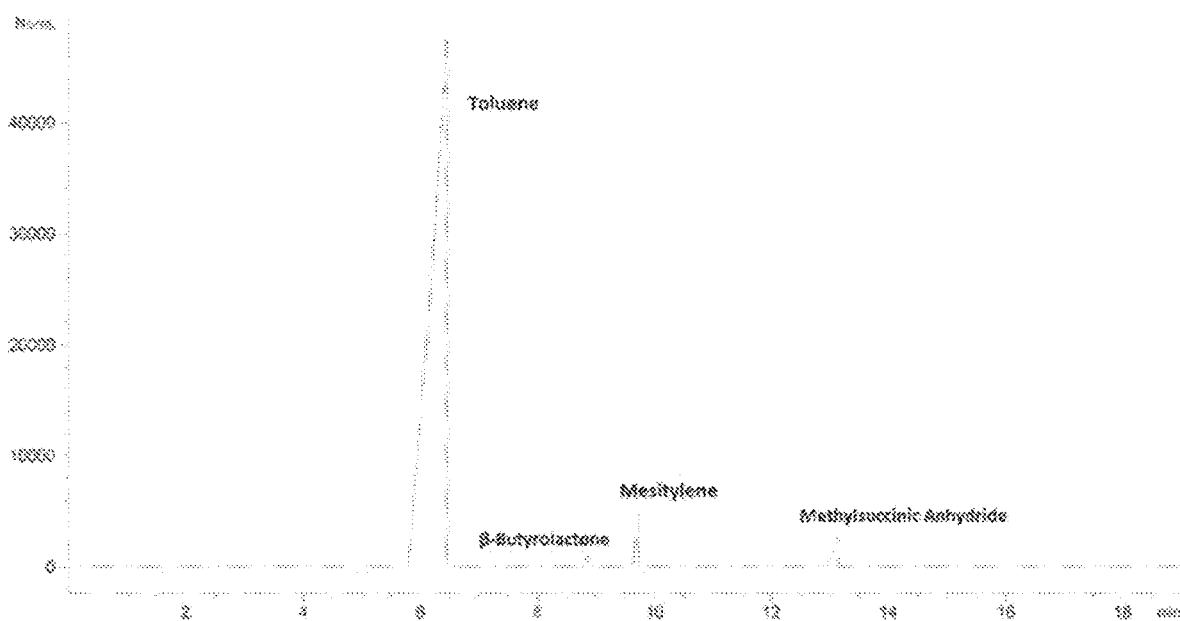
FIG. 4 shows a graphical representation of succinic anhydride formation from a β-lactone, according to one or more non-limiting embodiments.

For example, the β-lactone may be further carbonylated to form a particular product (e.g., succinic anhydrides). Alternatively, the formed β-lactone may be further catalyzed through different reaction mechanism and with the use of alternative catalysts, as known to one of ordinary skill in the art, to produce reaction products including, without limitation acrylates and hydroxyalkanoates.

β-lactone may be formed via carbonylation of an epoxide (e.g., using the methods described herein) or may be formed via different methods. According to some embodiments, the substrate β-lactone comprises a species as shown in Formula (II). In some embodiments, the product formed via carbonylation of a Formula (II) species comprises Formula (III):

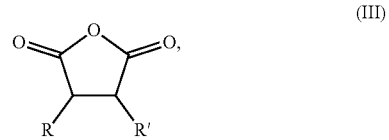
(III)

wherein R and R' are as described above in connection with Formula (I) (as shown in FIG. 4).

Figure 5:
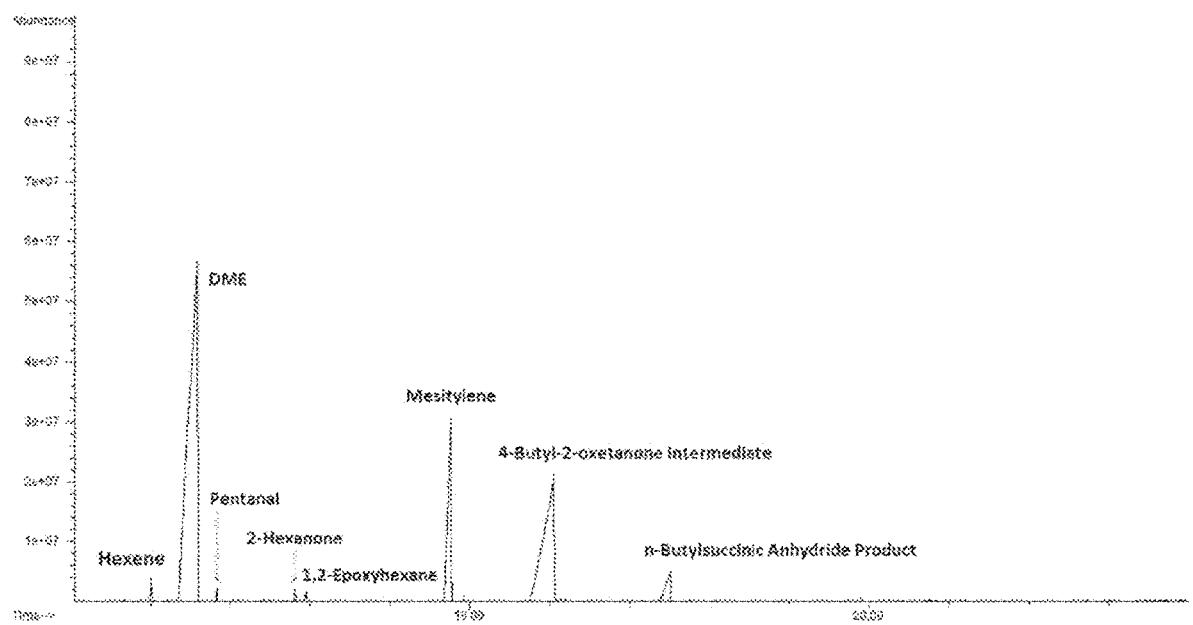
FIG. 5 shows a graphical representation of succinic anhydride formation from an epoxide, according to one or more non-limiting embodiments.

In some embodiments, the epoxide substrate comprising the structure as in Formula (I) may be carbonylated twice to form a compound comprising Formula (III) (as shown in FIG. 5). In some such embodiments, the epoxide substrate comprising the structure as in Formula (I) may undergo a first step of carbonylation, wherein the epoxide substrate may be almost completely converted to β-lactone comprising the structure as in Formula (II). A second step of carbonylation may then follow, in which the converted β-lactone may serve as the substrate in the carbonylation to a species comprising the structure as in Formula (III). Such two-step carbonylation processes may take place in a single reactor or in two separate reactors. Where both carbonylation steps take place in the same reactor, longer exposure times may be incorporated to provide sufficient time for both steps. In some embodiments, the temperature and/or pressure conditions may remain the same for both carbonylation steps. In some embodiments, the temperature and/or pressure conditions may be modified between the first carbonylation step and the second carbonylation step. Even when a modification is employed, however, the temperature and pressure generally remains within the ranges given for the initial epoxide carbonylation reaction, disclosed below.

In some embodiments, a substrate comprises Formula (IV):

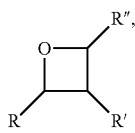

(IV)

wherein R, R' and R" may be the same or different and are hydrogen, an optionally substituted aliphatic group, an optionally substituted heteroaliphatic group, or an optionally substituted aromatic groups, or alternatively, R and R' may join to form an optionally substituted alicyclic compound. In some embodiments, the product formed via carbonylation of a Formula (IV) comprises a Formula (V):

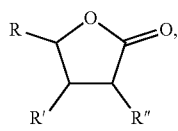

(V)

wherein R, R' and R" are as described above in connection with Formula (IV). In some embodiments, a substrate comprises Formula (VI):

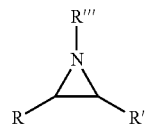

(VI)

wherein R and R' may be the same or different and are hydrogen, an optionally substituted aliphatic group, an optionally substituted heteroaliphatic group, or an optionally substituted aromatic groups, or alternatively, R and R' may join to form an optionally substituted alicyclic compound, and R''' is hydrogen, an optionally substituted aliphatic group, an optionally substituted heteroaliphatic group, or an optionally substituted aromatic groups, or a nitrogen protecting group. In some embodiments, the product formed via carbonylation of a Formula (VI) comprises a Formula (VII):

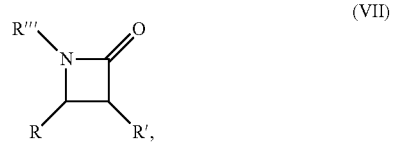

(VII)

wherein R, R', and R''' are as described above in connection with Formula (VI).

In some embodiments, a substrate comprises Formula (VIII):

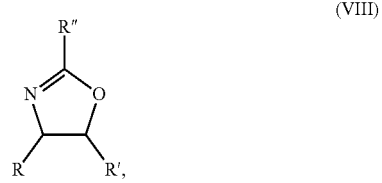

(VIII)

wherein R, R' and R" may be the same or different and are hydrogen, an optionally substituted aliphatic group, an optionally substituted heteroaliphatic group, or an optionally substituted aromatic groups, or alternatively, R and R' may join to form an optionally substituted alicyclic compound. In some embodiments, the product formed via carbonylation of a Formula (VIII) comprises a Formula (IX):

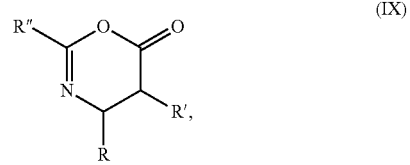

(IX)

wherein R, R', and R" are as described above in connection with Formula (IV).

In some embodiments, for the compounds of Formula (I)-(IX) described above, R, R' and R" may be the same or different and selected from the group consisting of hydrogen, optionally substituted alkyl, optionally substituted alkylene, optionally substituted alkylyne, optionally substituted heteroalkyl, optionally substituted arylalkyl, optionally substituted alkylaryl, and optionally substituted aryl. In some embodiments, at least one of R, R' and R" is hydrogen. In some embodiments, at least one of R, R' and R" is hydrogen and at least one of the others is optionally substituted alkyl. In some embodiments, R is hydrogen and at least one of R' and R" is optionally substituted alkyl. In some embodiments at least one of R' and R" is haloalkyl or alkoxylalkyl. In some embodiments, at least one of R' and R" is hydrogen and R is optionally substituted alkyl.

In some embodiments, for the compounds of Formula (VI)-(VII), R''' may be the same or different and selected from the group consisting of hydrogen, optionally substituted alkyl, optionally substituted alkylene, optionally substituted alkylyne, optionally substituted heteroalkyl, optionally substituted arylalkyl, optionally substituted alkylaryl, optionally substituted aryl, or a nitrogen-protecting group. In some embodiments, R''' is hydrogen. In some embodiments, R''' is optionally substituted alkyl. In some embodiments, R''' is optionally substituted aryl. In some embodiments, R''' is a nitrogen-protecting group.

The carbonylation reactions described herein may be performed under any suitable conditions, including by not limited to any suitable temperature, pressure, catalyst loading, and/or solvent conditions. In some embodiments, the reaction is carried out in a suitable apparatus capable of withstanding high pressures. In some embodiments, a catalyst and reactants described herein may be loaded into a reactor in any sequential order. The reactor may be charged with CO. Optionally, the reactor may contain one or more solvents (e.g., an organic solvent) and/or one or more additives. The reactor may be operated at any suitable temperature and/or pressure as described herein. In some embodiments, the reactor may be operated until a particular fraction (e.g., greater than about 50%, greater than about 60%, greater than about 70%, greater than about 75%, greater than about 90%, greater than about 95%, or more) of the substrate is converted to the desired product (e.g., β-lactones or succinic anhydrides). It should be understood, that in some embodiments, low conversion with high selectivity may be sufficient depending on the application, and no particular minimum threshold of substrate conversion need be met. However, in some embodiments, the reaction may proceed with both high conversion and high selectivity.

The heterogeneous catalyst (e.g., comprising an MOF and a plurality of $Co(CO)_4^-$ anions) may be provided in any suitable amount. In some embodiments, the ratio of the moles of substrate to the mole of cobalt in the catalyst may between about 10:1 and about 500:1, or between about 10:1 and about 400:1, or between about 10:1 and about 300:1, or between about 20:1 and about 300:1, or between about 20:1 and 200:1, or greater than about or about 10:1, or greater than about or about 20:1, or greater than about or about 50:1, or greater than about or about 100:1, or greater than about or about 150:1, or greater than about or about 200:1. Those of ordinary skill in the art will be aware of methods for determining the amount of cobalt in the catalyst, for example, using inductively coupled plasma mass spectrometer.

In some embodiments, the reactor is operated at a suitable pressure (e.g., at a pressure of 60 bar of CO). In some embodiments, the pressure of CO in the reactor is between 1 bar and 100 bar, between 10 bar and 90 bar, between 20 bar and 80 bar, between 40 bar and 75 bar, or between 50 bar and 70 bar. Other pressures may also be applied.

The reaction may be conducted at any suitable temperature. For example, in some cases, the reaction in the presence of the MOF may be conducted at about room temperature, for example, about 20° C., or higher, for example, between about 20° C. and about 100° C., between 30° C. and 95° C., between 40° C. and 90° C., between 50° C. and 90° C., between 60° C. and 90° C., or between 50° C. and 70° C. In other embodiments, the reaction may be carried out at different temperatures.

Additional details will now be described relating to MOFs and the composition comprising an MOF and a plurality of $Co(CO)_4^-$ anions. In some embodiments, the composition comprising an MOF and a plurality of $Co(CO)_4^-$ anions is utilized as a heterogeneous catalyst in the synthetic methods described herein. In some embodiments, the MOF comprises a plurality of metal ions, as least a portion of which are associate with a $Co(CO)_4^-$ anion. In some embodiments, methods of synthesizing a composition comprising an MOF and a plurality of $Co(CO)_4^-$ anions (e.g., for use as a heterogeneous catalyst) are provided. The method may comprise exposing a metal organic framework (MOF) comprising a plurality of metal ions, each coordinated with at least one ligand, to a solution comprising a plurality of $Co(CO)_4^-$ anions, thereby forming a composition comprising the MOF having at least a portion of the metal ions associated with a $Co(CO)_4^-$ anion.

The term "metal-organic framework" is given its ordinary meaning in the art and refers to a one-, two-, or three-dimensional coordination polymer including metal ions and ligands which function as organic structural units, wherein a portion of the metal ions are each chemically bonded to at least one ligand comprising a bi-, tri- or poly-dentate organic structural unit The metal ions, in addition to being coordinated with at least one ligand, may also be bound to one or more auxiliary ligands, as described in more detail herein In some embodiments, a MOF comprises a plurality of metal ions, each coordinated with at least one ligand In some embodiments, at least some of the metal ions are associated with two, three, or four ligands In some embodiments, each of those ligands are individually associated with one, two, three, or four metal ions.

In some embodiments a plurality of precursor charge-balancing anions may be associated with the MOF, prior to introduction of $Co(CO)_4^-$ anions. Non-limiting examples of precursor anions include halides (e.g., chlorine, fluorine, bromine, iodine), triflate, $NO_3^-$, $SO_4^{2-}$, $ClO_4^-$, nitrate, carbonate, sulfonate, etc. In some embodiments, a portion of the precursor anions may be replaced by the $Co(CO)_4^-$ anions.

According to some embodiments the precursor anions may be replaced with a plurality of intermediary anions prior to the introduction of $Co(CO)_4^-$ anions. The intermediary anions may, for example, comprise $Cl^-$. The intermediary anions may be introduced via a solution comprising a source of the intermediary anions. For example, the solution may comprise an intermediary compound (e.g., $AlCl_3$) that both reacts with the precursor anions (e.g., $F^-$) to displace them from the MOF and serves as a source of intermediary anions (e.g., $Cl^-$).

The intermediary compound may, for example, comprise a species capable of serving as a source of metal cations (e.g., $Al^{3+}$) having a charge of (3+) or greater, and as a source of intermediary anions that balance out the charge of the metal cations (e.g., halides, triflate, $NO_3^-$, $SO_4^{2-}$, $ClO_4^-$, nitrate, acetate, carbonate, sulfonate, etc.). The metal cations (e.g., $Al^{3+}$) provided by the intermediary compound may show a greater affinity for the precursor anions than the framework metal cations (e.g., $Cr^{3+}$) of the MOF do, and therefore cause the precursor anions (e.g., $F^-$) to disassociate from the MOF. In some embodiments, metal cations (e.g., $Al^{3+}$) provided by the intermediary compound may have an ionic radius smaller than that of the framework metal cations (e.g., $Cr^{3+}$) of the MOF. The intermediary anions provided by the intermediary compound may then become associated with the MOF. A non-limiting example of this intermediary step is described in Example 1, below.

According to some embodiments, a solution comprising a plurality of $Co(CO)_4^-$ anions, may then be introduced to the MOF. The plurality of $Co(CO)_4^-$ anions may be introduced as a member of a solution comprising a salt (e.g., Na[Co$(CO)_4$]). The salt may comprise the $Co(CO)_4^-$ anions and any suitable counterion (e.g., $Na^+$) and any non-reactive metal/organic cationic species may generally suffice, as long as the $Co(CO)_4^-$ anions dissolve in the exchange solvent. According to certain embodiments, the plurality of $Co(CO)_4^-$ anions may displace the intermediary anions or the precursor anions from the MOF, to produce a composition comprising the MOF and the plurality of $Co(CO)_4^-$ anions associated with the MOF. As described in the non-limiting embodiment of this process presented in Example 6, below, the replacement of intermediary anions (e.g., Cl⁻) associated with the MOF with Co(CO)$_4^-$ anions, may be carried out at room temperature, and atmospheric pressure, at a ratio of Co(CO)$_4^-$ anions to intermediary and/or precursor anions sufficient to substantially replace the intermediary and/or precursor anions with Co(CO)$_4^-$. In some embodiments, the cobalt compound is provided in an equimolar or greater amount of the cobalt compound to the precursor and/or intermediary anions of the MOF. Furthermore, it should be understood that the exchange of anions may take place under any suitable conditions, as would be understood by a person of ordinary skill in the art. For example, the synthesis and/or manipulation steps that involve the cobalt carbonyl compound may take place under conditions substantially free of O$_2$.

In some embodiments, prior to use in a catalytic reaction, the compositions described herein (e.g., comprising an MOF and a plurality of Co(CO)$_4^-$ anions) may be purified using techniques known to those of ordinary skill in the art. In some embodiments, a synthesized MOF may be washed, sometimes involving a Soxhlet extractor, boiled, and/or sonicated (e.g., to remove excess starting materials).

The MOF may comprise any suitable metal ions or any combination of suitable metal ions. Examples of suitable metal ions include, without limitation, Cr$^{3+}$, Al$^{3+}$, Sc$^{3+}$, Fe$^{3+}$, Ti$^{3+}$. Each metal ion may be monovalent, divalent, trivalent, or tetravalent. In some embodiments, a least one type of metal ion is a monovalent metal ion. Non-limiting examples of monovalent metal ions are Ag$^+$, Cu$^+$, and Au$^+$. In some embodiments, at least one type of metal ion is a divalent metal ion. Non-limiting examples of monovalent metal ions are Mg$^{2+}$, Mn$^{2+}$, Fe$^{2+}$, Co$^{2+}$, Ni$^{2+}$, Cu$^{2+}$, Pd$^{2+}$, Pt$^{2+}$, Ru$^{2+}$, Cd$^{2+}$, Zn$^{2+}$, Pb$^{2+}$, Hg$^{2+}$, V$^{2+}$, and Cr$^{2+}$. In some embodiments, at least one type of metal ion is a trivalent metal ion. Non-limiting examples of trivalent metal ions are Fe$^{3+}$, V$^{3+}$, Ti$^{3+}$, Sc$^{3+}$, Al$^{3+}$, In$^{3+}$, Ga$^{3+}$, Mn$^{3+}$, Co$^{3+}$, and Cr$^{3+}$. In some embodiments, at least one type of metal ion is a tetravalent metal ion. A non-limiting example of tetravalent metal ion is Ti$^{4+}$ and Zn$^{4+}$.

In some embodiments, each MOF comprises more than one of the first type of metal ion. In some embodiments, one or more of the first type of metal ion are the active metal centers for catalysis. In some embodiments, only a single first type of metal ion is an active metal center for catalysis.

In some embodiments, the MOFs formed may comprise little or no excess metal ions. That is, the MOF comprises essentially no metal ions which are not coordinated with a ligand (i.e., "free metal ions"). In some embodiments, the MOF comprises less than about 0.5 wt %, or less then about 0.4 wt %, or less then about 0.3 wt %, or less than about 0.2 wt %, or less then about 0.1 wt %, or less than about 0.05 wt %, or less than about 0.03 wt %, or less than about 0.02 wt %, or less than about 0.01 wt %, or less than about 0.005 wt %, or less than about 0.001 wt % of free metal ions. Those of ordinary skill in the art will be aware of methods for determining the amount of free metal ions, for example, using XPS.

According to some embodiments, one or more ligands of the MOF may comprise one or more aromatic groups (e.g., benzene groups). According to some embodiments, one or more ligands of the MOF may comprise one or more carboxylate groups. In some embodiments the one or more carboxylate groups may be bonded to one or more aromatic groups. According to some embodiments, each metal ion is coordinated with its associated one or more ligands at a carboxylate group of that ligand, as shown, for example, in FIG. 6, discussed further herein. In some embodiments, the ligands may comprise phthalic acid (e.g. terephthalic acid). In alternative embodiments, the MOF may comprise non-carboxylate ligands.

In some cases, each metal ion is coordinated with at least two ligands, at least three ligands, or at least four ligands. For example, in some embodiments, the MOF comprises a plurality of metal ions associated with at least two carboxylate groups, at least three carboxylate groups, or at least four carboxylate groups. Other non-limiting examples of suitable ligands are described in detail herein. In some embodiments, a ligand is charged. In some embodiments, a ligand has a charge of (−1), or (−2), or (−3), or (−4).

In some embodiments, each ligand has the structure [Q-(COO)$_m$]$^{m-}$, wherein, Q is an organic core, m is 2, 3, or 4, and COO is a carboxylate group. In some embodiments, each m is 2. In some embodiments, each m is 3. In some embodiments, each m is 4. In some embodiments, each ligand has the structure [Q-(COO)$_2$]$^{2-}$, wherein, Q is an organic core. In some embodiments, Q comprises an aromatic group (e.g., phenyl) or a plurality of fused aryl and/or heteroaryl rings. In some embodiments, Q comprises the structure:

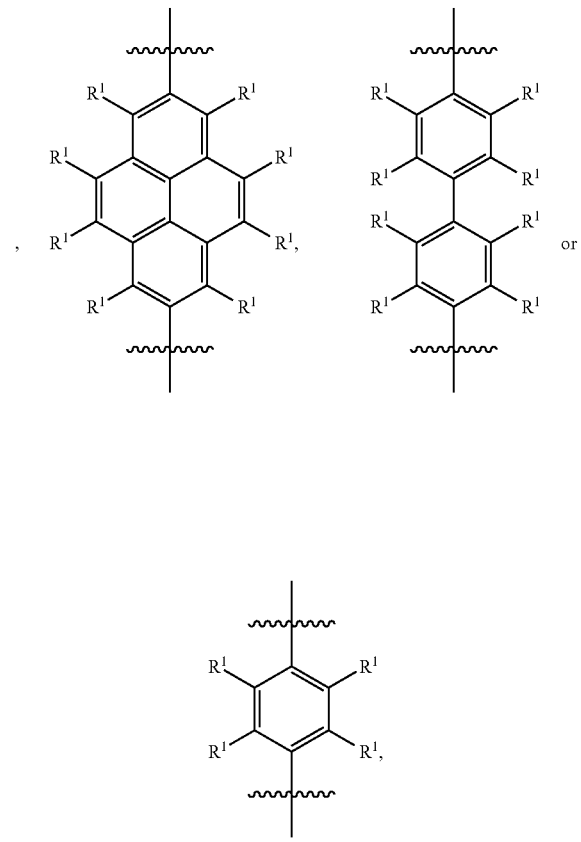

wherein each R$^1$ is the same or different and is selected from the group consisting of hydrogen, —NO$_2$, —R$^2$, —F, —Cl, —Br, —I, —CN, —NC, —SO$_3$R$^2$, —SO$_3$H, —OR$^2$, —OH, —SR$^2$, —SH, —PO$_3$R$^2$, —PO$_3$H, —CF$_3$, —N(R$^2$)$_2$, —NHR$^2$, and —NH$_2$, wherein each R$^2$ is the same or different and is optionally substituted alkyl or optionally substituted aryl. In some embodiments, Q comprises the structure:

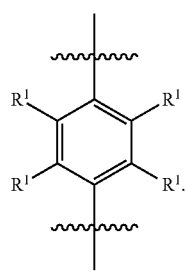

wherein each $R^1$ is as described above. In some embodiments, Q comprises the structure:

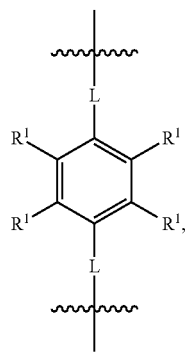

wherein each $R^1$ is as described above and wherein each L is the same or different and is a suitable linking group, for example, optionally subsituted alkylene, optionally substituted heteroalkylene, optionally substituted arylene, or optionally substituted heteroarylene.

In some embodiments, each $R^1$ is hydrogen or optionally substituted alkyl. In some embodiments, each $R^1$ is hydrogen.

Figure 6:
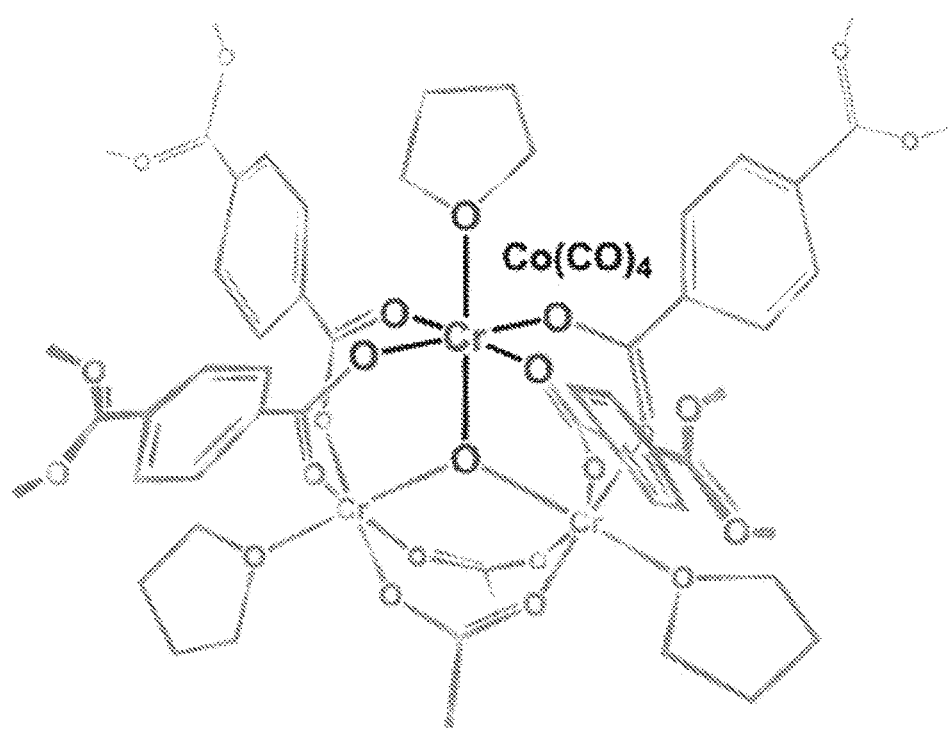
FIG. 6 shows an illustration of the structure of a metal organic framework, according to one or more non-limiting embodiments.

In some embodiments, the MOF has a structure as shown in FIG. 6. In the embodiment shown in FIG. 6, the MOF comprises Cr-MIL-101 ($Cr_3O(BDC)_3$, $H_2BDC$=1,4-benzene-di-carboxylic acid (terephthalic acid)). The metal clusters of Cr-MIL-101 contain Cr(III) octahedra that are coordinated equatorially by the oxygen atoms of the bridging terephthalate ligands and axially by a $\mu_3$-oxygen atom and a solvent molecule, as shown in FIG. 6. At a precursor stage, Cr-MIL-101 has a cationic framework with ion-exchangeable $F^-$, allowing for the possibility of $Co(CO)_4^-$ incorporation to form a heterogeneous catalyst of the general formula [Lewis acid]$^+$[Co(CO)$_4$]$^-$. Other favorable innate properties of Cr-MIL-101 include its high hydrothermal and chemical stability, large windows (12 Å and 14.5 Å×16 Å) and pores (29 Å and 34 Å) for ready diffusion of reaction species, and facile synthesis using inexpensive chromium and terephthalic acid precursors.

In some embodiments, each metal ion in the MOF may be associated with one or more auxiliary ligands. In some cases, the one or more auxiliary ligands may be found above and/or below the metal ion (e.g., as apical ligands). An auxiliary ligand may or might not be charged. Non-limiting examples of auxiliary ligands include halides (e.g., chlorine, fluorine, bromine, iodine), other salts (e.g., alkyl (e.g., —$CH_3$), allyl, nitrite, sulfite, chloride, fluoride, bromide, iodide, triflate, $BF_4$, $PF_6$, $NO_4^{2-}$, $ClO_4^-$, nitrate, carbonate, sulfonate, etc.), and coordinating solvents (e.g., water, pyridine, tetrahydrofuran, diethyl ether, tetrahydrofuran, ammonia, toluene, benzene, etc.).

Any suitable solvent may be optionally utilized in the synthetic methods of forming the MOFs to compositions comprising the MOFs and a plurality of $Co(CO)_4^-$ anions described herein. Non-limiting examples of solvents include water, methanol, ethanol, propanol, benzene, p-cresol, toluene, xylene, diethyl ether, glycol, diethyl ether, petroleum ether, hexane, cyclohexane, pentane, methylene chloride, chloroform, carbon tetrachloride, dioxane, tetrahydrofuran (THF), dimethyl sulfoxide (DMSO), dimethylformamide, hexamethyl-phosphoric triamide, ethyl acetate, pyridine, triethylamine, picoline, mixtures thereof, or the like.

MOFs may be synthesized using methods known in the art (e.g., see Chem Eur J 2011, 17, 1837-1848; Chem Eur J 2015, 21, 8188-8199) For example, in some cases, a method of synthesizing a MOF comprises exposing a plurality of metal ions to a plurality of precursor ligands to form the MOF comprising a portion of the plurality of metal ions each coordinated with at least one ligand. The metal ions and the ligand may be provided in any suitable amounts. In some embodiments, the mole ratio of the metal ion to the ligand may be based upon the coordination of the metal ion to the ligand. For example, in some embodiments, where the ligand is coordinated with three metal ions, and each metal ion is associated with two ligands, the mole ratio of the metal ion to the ligand may be at least 3:2 As another example, in embodiments, where the ligand is coordinated with two metal ions, and each metal ion is associated with one ligand, the mole ratio of the metal ion to the precursor ligand may about 2:1 In some embodiments, the ligand is provided in slight molar excess.

Definitions

For convenience, certain terms employed in the specification, examples, and appended claims are listed here.

As used herein, the term "reacting" refers to the forming of a bond between two or more components to produce a stable, isolable compound. For example, a first component and a second component may react to form one reaction product comprising the first component and the second component joined by a covalent bond. That is, the term "reacting" does not refer to the interaction of solvents, catalysts, bases, ligands, or other materials which may serve to promote the occurrence of the reaction with the component(s).

Definitions of specific functional groups and chemical terms are described in more detail below. For purposes of this invention, the chemical elements are identified in accordance with the Periodic Table of the Elements, CAS version, *Handbook of Chemistry and Physics*, 75$^{th}$ Ed., inside cover, and specific functional groups are generally defined as described therein. Additionally, general principles of organic chemistry, as well as specific functional moieties and reactivity, are described in *Organic Chemistry*, Thomas Sorrell, University Science Books, Sausalito: 1999, the entire contents of which are incorporated herein by reference.

The term "aliphatic," as used herein, includes both saturated and unsaturated, nonaromatic, straight chain (i.e., unbranched), branched, acyclic, and cyclic (i.e., carbocyclic) hydrocarbons, which are optionally substituted with one or more functional groups. As will be appreciated by one of ordinary skill in the art, "aliphatic" is intended herein to include, but is not limited to, alkyl, alkenyl, alkynyl, cycloalkyl, cycloalkenyl, and cycloalkynyl moieties. Thus, as used herein, the term "alkyl" includes straight, branched and cyclic alkyl groups. An analogous convention applies to other generic terms such as "alkenyl", "alkynyl", and the like. Furthermore, as used herein, the terms "alkyl", "alkenyl", "alkynyl", and the like encompass both substituted and unsubstituted groups. In certain embodiments, as used herein, "aliphatic" is used to indicate those aliphatic groups (cyclic, acyclic, substituted, unsubstituted, branched or unbranched) having 1-20 carbon atoms. Aliphatic group substituents include, but are not limited to, any of the substituents described herein, that result in the formation of a stable moiety (e.g., aliphatic, alkyl, alkenyl, alkynyl, heteroaliphatic, heterocyclic, aryl, heteroaryl, acyl, oxo, imino, thiooxo, cyano, isocyano, amino, azido, nitro, hydroxyl, thiol, halo, aliphaticamino, heteroaliphaticamino, alkylamino, heteroalkylamino, arylamino, heteroarylamino, alkylaryl, arylalkyl, aliphaticoxy, heteroaliphaticoxy, alkyloxy, heteroalkyloxy, aryloxy, heteroaryloxy, aliphaticthioxy, heteroaliphaticthioxy, alkylthioxy, heteroalkylthioxy, arylthioxy, heteroarylthioxy, acyloxy, and the like, each of which may or may not be further substituted).

As used herein, the term "alkyl" is given its ordinary meaning in the art and refers to the radical of saturated aliphatic groups, including straight-chain alkyl groups, branched-chain alkyl groups, cycloalkyl (alicyclic) groups, alkyl substituted cycloalkyl groups, and cycloalkyl substituted alkyl groups. In some cases, the alkyl group may be a lower alkyl group, i.e., an alkyl group having 1 to 10 carbon atoms (e.g., methyl, ethyl, propyl, butyl, pentyl, hexyl, heptyl, octyl, nonyl, or decyl). In some embodiments, a straight chain or branched chain alkyl may have 30 or fewer carbon atoms in its backbone, and, in some cases, 20 or fewer. In some embodiments, a straight chain or branched chain alkyl may have 12 or fewer carbon atoms in its backbone (e.g., $C_1$-$C_{12}$ for straight chain, $C_3$-$C_{12}$ for branched chain), 6 or fewer, or 4 or fewer. Likewise, cycloalkyls may have from 3-10 carbon atoms in their ring structure, or 5, 6 or 7 carbons in the ring structure. Examples of alkyl groups include, but are not limited to, methyl, ethyl, propyl, isopropyl, cyclopropyl, butyl, isobutyl, t-butyl, cyclobutyl, hexyl, and cyclohexyl.

The term "alkylene" as used herein refers to a bivalent alkyl group. An "alkylene" group is a polymethylene group, i.e., —$(CH_2)_z$—, wherein z is a positive integer, e.g., from 1 to 20, from 1 to 10, from 1 to 6, from 1 to 4, from 1 to 3, from 1 to 2, or from 2 to 3. A substituted alkylene chain is a polymethylene group in which one or more methylene hydrogen atoms are replaced with a substituent. Suitable substituents include those described herein for a substituted aliphatic group.

Generally, the suffix "-ene" is used to describe a bivalent group. Thus, any of the terms defined herein can be modified with the suffix "-ene" to describe a bivalent version of that moiety. For example, a bivalent carbocycle is "carbocyclylene", a bivalent aryl ring is "arylene", a bivalent benzene ring is "phenylene", a bivalent heterocycle is "heterocyclylene", a bivalent heteroaryl ring is "heteroarylene", a bivalent alkyl chain is "alkylene", a bivalent alkenyl chain is "alkenylene", a bivalent alkynyl chain is "alkynylene", a bivalent heteroalkyl chain is "heteroalkylene", a bivalent heteroalkenyl chain is "heteroalkenylene", a bivalent heteroalkynyl chain is "heteroalkynylene", and so forth.

The terms "alkenyl" and "alkynyl" are given their ordinary meaning in the art and refer to unsaturated aliphatic groups analogous in length and possible substitution to the alkyls described above, but that contain at least one double or triple bond respectively.

In certain embodiments, the alkyl, alkenyl and alkynyl groups employed in the invention contain 1-20 aliphatic carbon atoms. In certain other embodiments, the alkyl, alkenyl, and alkynyl groups employed in the invention contain 1-10 aliphatic carbon atoms. In yet other embodiments, the alkyl, alkenyl, and alkynyl groups employed in the invention contain 1-8 aliphatic carbon atoms. In still other embodiments, the alkyl, alkenyl, and alkynyl groups employed in the invention contain 1-6 aliphatic carbon atoms. In yet other embodiments, the alkyl, alkenyl, and alkynyl groups employed in the invention contain 1-4 carbon atoms. Illustrative aliphatic groups thus include, but are not limited to, for example, methyl, ethyl, n-propyl, isopropyl, allyl, n-butyl, sec-butyl, isobutyl, t-butyl, n-pentyl, sec-pentyl, isopentyl, t-pentyl, n-hexyl, sec-hexyl, moieties and the like, which again, may bear one or more substituents. Alkenyl groups include, but are not limited to, for example, ethenyl, propenyl, butenyl, 1-methyl-2-buten-1-yl, and the like. Representative alkynyl groups include, but are not limited to, ethynyl, 2-propynyl (propargyl), 1-propynyl and the like.

The term "alkoxyalkyl" refers to an alkyl group substituted with at least one alkoxy group (e.g., one, two, three, or more, alkoxy groups). For example, an alkoxyalkyl group may be —($C_{1-6}$-alkyl)-O—($C_{1-6}$-alkyl), optionally substituted. In some cases, the alkoxyalkyl group may be optionally substituted with another alkyoxyalkyl group (e.g., —($C_{1-6}$-alkyl)-O—($C_{1-6}$-alkyl)-O—($C_{1-6}$-alkyl), optionally substituted.

The term "cycloalkyl," as used herein, refers specifically to groups having three to ten, preferably three to seven carbon atoms. Suitable cycloalkyls include, but are not limited to cyclopropyl, cyclobutyl, cyclopentyl, cyclohexyl, cycloheptyl and the like, which, as in the case of other aliphatic, heteroaliphatic, or hetercyclic moieties, may optionally be substituted with substituents including, but not limited to aliphatic; heteroaliphatic; aryl; heteroaryl; arylalkyl; heteroarylalkyl; alkoxy; aryloxy; heteroalkoxy; heteroaryloxy; alkylthio; arylthio; heteroalkylthio; heteroarylthio; —F; —Cl; —Br; —I; —OH; —$NO_2$; —CN; —$CF_3$; —$CH_2CF_3$; —$CHCl_2$; —$CH_2OH$; —$CH_2CH_2OH$; —$CH_2NH_2$; —$CH_2SO_2CH_3$; —$C(O)R_x$; —$CO_2(R_x)$; —$CON(R_x)_2$; —$OC(O)R_x$; —$OCO_2R_x$; —$OCON(R_x)_2$; —$N(R_x)_2$; —$S(O)_2R_x$; —$NR_x(CO)R_x$, wherein each occurrence of $R_x$ independently includes, but is not limited to, aliphatic, heteroaliphatic, aryl, heteroaryl, arylalkyl, or heteroarylkyl, wherein any of the aliphatic, heteroaliphatic, arylalkyl, or heteroarylalkyl substituents described above and herein may be substituted or unsubstituted, branched or unbranched, cyclic or acyclic, and wherein any of the aryl or heteroaryl substituents described above and herein may be substituted or unsubstituted. Additional examples of generally applicable substituents are illustrated by the specific embodiments shown in the Examples that are described herein.

The term "heteroaliphatic," as used herein, refers to an aliphatic moiety, as defined herein, which includes both saturated and unsaturated, nonaromatic, straight chain (i.e., unbranched), branched, acyclic, cyclic (i.e., heterocyclic), or polycyclic hydrocarbons, which are optionally substituted with one or more functional groups, and that contain one or more oxygen, sulfur, nitrogen, phosphorus, or silicon atoms, e.g., in place of carbon atoms. In certain embodiments, heteroaliphatic moieties are substituted by independent replacement of one or more of the hydrogen atoms thereon with one or more substituents. As will be appreciated by one of ordinary skill in the art, "heteroaliphatic" is intended herein to include, but is not limited to, heteroalkyl, heteroalkenyl, heteroalkynyl, heterocycloalkyl, heterocycloalkenyl, and heterocycloalkynyl moieties. Thus, the term "heteroaliphatic" includes the terms "heteroalkyl," "heteroalkenyl", "heteroalkynyl", and the like. Furthermore, as used herein, the terms "heteroalkyl", "heteroalkenyl", "heteroalkynyl", and the like encompass both substituted and unsubstituted groups. In certain embodiments, as used herein, "heteroaliphatic" is used to indicate those heteroaliphatic groups (cyclic, acyclic, substituted, unsubstituted, branched or unbranched) having 1-20 carbon atoms. Heteroaliphatic group substituents include, but are not limited to, any of the substituents described herein, that result in the formation of a stable moiety (e.g., aliphatic, alkyl, alkenyl, alkynyl, heteroaliphatic, heterocyclic, aryl, heteroaryl, acyl, sulfinyl, sulfonyl, oxo, imino, thiooxo, cyano, isocyano, amino, azido, nitro, hydroxyl, thiol, halo, aliphaticamino, heteroaliphaticamino, alkylamino, heteroalkylamino, arylamino, heteroarylamino, alkylaryl, arylalkyl, aliphaticoxy, heteroaliphaticoxy, alkyloxy, heteroalkyloxy, aryloxy, heteroaryloxy, aliphaticthioxy, heteroaliphaticthioxy, alkylthioxy, heteroalkylthioxy, arylthioxy, heteroarylthioxy, acyloxy, and the like, each of which may or may not be further substituted).

The term "heteroalkyl" is given its ordinary meaning in the art and refers to an alkyl group as described herein in which one or more carbon atoms is replaced by a heteroatom. Suitable heteroatoms include oxygen, sulfur, nitrogen, phosphorus, and the like. Examples of heteroalkyl groups include, but are not limited to, alkoxy, alkoxyalkyl, amino, thioester, poly(ethylene glycol), and alkyl-substituted amino.

The terms "heteroalkenyl" and "heteroalkynyl" are given their ordinary meaning in the art and refer to unsaturated aliphatic groups analogous in length and possible substitution to the heteroalkyls described above, but that contain at least one double or triple bond respectively.

Some examples of substituents of the above-described aliphatic (and other) moieties of compounds of the invention include, but are not limited to aliphatic; heteroaliphatic; aryl; heteroaryl; alkylaryl; alkylheteroaryl; alkoxy; aryloxy; heteroalkoxy; heteroaryloxy; alkylthio; arylthio; heteroalkylthio; heteroarylthio; F; Cl; Br; I; —OH; —NO$_2$; —CN; —CF$_3$; —CHF$_2$; —CH$_2$F; —CH$_2$CF$_3$; —CHCl$_2$; —CH$_2$OH; —CH$_2$CH$_2$OH; —CH$_2$NH$_2$; —CH$_2$SO$_2$CH$_3$; —C(O)R$_x$; —CO$_2$(R$_x$); —CON(R$_x$)$_2$; —OC(O)R$_x$; —OCO$_2$R$_x$; —OCON(R$_x$)$_2$; —N(R$_x$)$_2$; —S(O)$_2$R$_x$; —NR$_x$(CO)R$_x$ wherein each occurrence of R$_x$ independently includes, but is not limited to, aliphatic, alycyclic, heteroaliphatic, heterocyclic, aryl, heteroaryl, alkylaryl, or alkylheteroaryl, wherein any of the aliphatic, heteroaliphatic, alkylaryl, or alkylheteroaryl substituents described above and herein may be substituted or unsubstituted, branched or unbranched, cyclic or acyclic, and wherein any of the aryl or heteroaryl substituents described above and herein may be substituted or unsubstituted. Additional examples of generally applicable substituents are illustrated by the specific embodiments shown in the Examples that are described herein.

The term "aryl" is given its ordinary meaning in the art and refers to aromatic carbocyclic groups, optionally substituted, having a single ring (e.g., phenyl), multiple rings (e.g., biphenyl), or multiple fused rings in which at least one is aromatic (e.g., 1,2,3,4-tetrahydronaphthyl, naphthyl, anthryl, or phenanthryl). That is, at least one ring may have a conjugated pi electron system, while other, adjoining rings can be cycloalkyls, cycloalkenyls, cycloalkynyls, aryls and/or heterocyclyls. The aryl group may be optionally substituted, as described herein. Substituents include, but are not limited to, any of the previously mentioned substituents, i.e., the substituents recited for aliphatic moieties, or for other moieties as disclosed herein, resulting in the formation of a stable compound. In some cases, an aryl group is a stable mono- or polycyclic unsaturated moiety having preferably 3-14 carbon atoms, each of which may be substituted or unsubstituted. "Carbocyclic aryl groups" refer to aryl groups wherein the ring atoms on the aromatic ring are carbon atoms. Carbocyclic aryl groups include monocyclic carbocyclic aryl groups and polycyclic or fused compounds (e.g., two or more adjacent ring atoms are common to two adjoining rings) such as naphthyl groups.

The terms "heteroaryl" is given its ordinary meaning in the art and refers to aryl groups comprising at least one heteroatom as a ring atom. A "heteroaryl" is a stable heterocyclic or polyheterocyclic unsaturated moiety having preferably 3-14 carbon atoms, each of which may be substituted or unsubstituted. Substituents include, but are not limited to, any of the previously mentioned substituents, i.e., the substitutes recited for aliphatic moieties, or for other moieties as disclosed herein, resulting in the formation of a stable compound. In some cases, a heteroaryl is a cyclic aromatic radical having from five to ten ring atoms of which one ring atom is selected from S, O, and N; zero, one, or two ring atoms are additional heteroatoms independently selected from S, O, and N; and the remaining ring atoms are carbon, the radical being joined to the rest of the molecule via any of the ring atoms, such as, for example, pyridyl, pyrazinyl, pyrimidinyl, pyrrolyl, pyrazolyl, imidazolyl, thiazolyl, oxazolyl, isooxazolyl, thiadiazolyl, oxadiazolyl, thiophenyl, furanyl, quinolinyl, isoquinolinyl, and the like.

It will also be appreciated that aryl and heteroaryl moieties, as defined herein may be attached via an alkyl or heteroalkyl moiety and thus also include (alkyl)aryl, -(heteroalkyl)aryl, -(heteroalkyl)heteroaryl, and (heteroalkyl)heteroaryl moieties. Thus, as used herein, the phrases "aryl or heteroaryl moieties" and "aryl, heteroaryl, (alkyl)aryl, -(heteroalkyl)aryl, -(heteroalkyl)heteroaryl, and -(heteroalkyl)heteroaryl" are interchangeable. Substituents include, but are not limited to, any of the previously mentioned substituents, i.e., the substituents recited for aliphatic moieties, or for other moieties as disclosed herein, resulting in the formation of a stable compound.

It will be appreciated that aryl and heteroaryl groups (including bicyclic aryl groups) can be unsubstituted or substituted, wherein substitution includes replacement of one or more of the hydrogen atoms thereon independently with any one or more of the following moieties including, but not limited to: aliphatic; alicyclic; heteroaliphatic; heterocyclic; aromatic; heteroaromatic; aryl; heteroaryl; alkylaryl; heteroalkylaryl; alkylheteroaryl; heteroalkylheteroaryl; alkoxy; aryloxy; heteroalkoxy; heteroaryloxy; alkylthio; arylthio; heteroalkylthio; heteroarylthio; F; Cl; Br; I; —OH; —NO$_2$; —CN; —CF$_3$; —CH$_2$F; —CHF$_2$; —CH$_2$CF$_3$; —CHCl$_2$; —CH$_2$OH; —CH$_2$CH$_2$OH; —CH$_2$NH$_2$; —CH$_2$SO$_2$CH$_3$; —C(O)R$_x$; —CO$_2$(R$_x$); —CON(R$_x$)$_2$; —OC(O)R$_x$; —OCO$_2$R$_x$; —OCON(R$_x$)$_2$; —N(R$_x$)$_2$; —S(O)R$_x$; —S(O)$_2$R$_x$; —NR$_x$(CO)R$_x$ wherein each occurrence of R$_x$ independently includes, but is not limited to, aliphatic, alicyclic, heteroaliphatic, heterocyclic, aromatic, heteroaromatic, aryl, heteroaryl, alkylaryl, alkylheteroaryl, heteroalkylaryl or heteroalkylheteroaryl, wherein any of the aliphatic, alicyclic, heteroaliphatic, heterocyclic, alkylaryl, or alkylheteroaryl substituents described above and herein may be substituted or unsubstituted, branched or unbranched, saturated or unsaturated, and wherein any of the aromatic, heteroaromatic, aryl, heteroaryl, -(alkyl)aryl or -(alkyl)heteroaryl substituents described above and herein may be substituted or unsubstituted. Additionally, it will be appreciated, that any two adjacent groups taken together may represent a 4, 5, 6, or 7-membered substituted or unsubstituted alicyclic or heterocyclic moiety. Additional examples of generally applicable substituents are illustrated by the specific embodiments described herein.

The terms "halo" and "halogen" as used herein refer to an atom selected from the group consisting of fluorine, chlorine, bromine, and iodine. The term "nitrogen-protecting group" as given its ordinary meaning in the art and includes those groups described in detail in *Protecting Groups in Organic Synthesis*, T. W. Greene and P. G. M. Wuts, $3^{rd}$ edition, John Wiley & Sons, 1999, incorporated herein by reference. For example, nitrogen protecting groups include, but are not limited to, carbamates (including methyl, ethyl and substituted ethyl carbamates (e.g. Troc), to name a few), amides, cyclic imide derivatives, N-alkyl and N-aryl amines, imine derivatives, and enamine derivatives, to name a few. In some embodiments, the nitrogen-protecting group is carbobenzyloxy (Cbz), p-methoxybenzyl carbonyl (MeOZ), t-butyloxycarbonyl (Boc), 9-fluorenylmethyloxycarbonyl (Fmoc), acetyl (Ac), benzoyl (Bz), benzyl (Bn), p-methoxybenzyl (PMB), 3,4-dimethoxybenzyl (DMPM), p-methoxyphenyl (PMP), or p-toluenesulfonyloxy (Ts). In certain embodiments, at least one $R^2$ is t-butyloxycarbonyl (Boc).

Nitrogen-protecting groups such as amide groups include, but are not limited to, formamide, acetamide, chloroacetamide, trichloroacetamide, trifluoroacetamide, phenylacetamide, 3-phenylpropanamide, picolinamide, 3-pyridylcarboxamide, N-benzoylphenylalanyl derivative, benzamide, p-phenylbenzamide, o-nitrophenylacetamide, o-nitrophenoxyacetamide, acetoacetamide, (N'-dithiobenzyloxyacylamino)acetamide, 3-(p-hydroxyphenyl)propanamide, 3-(o-nitrophenyl)propanamide, 2-methyl-2-(o-nitrophenoxy) propanamide, 2-methyl-2-(o-phenylazophenoxy) propanamide, 4-chlorobutanamide, 3-methyl-3-nitrobutanamide, o-nitrocinnamide, N-acetylmethionine derivative, o-nitrobenzamide and o-(benzoyloxymethyl) benzamide.

Nitrogen-protecting groups such as carbamate groups include, but are not limited to, methyl carbamate, ethyl carbamate, 9-fluorenylmethyl carbamate (Fmoc), 9-(2-sulfo)fluorenylmethyl carbamate, 9-(2,7-dibromo)fluorenylmethyl carbamate, 2,7-di-t-butyl-[9-(10,10-dioxo-10,10, 10,10-tetrahydrothioxanthyl)]methyl carbamate (DBDT-Tmoc), 4-methoxyphenacyl carbamate (Phenoc), 2,2,2-trichloroethyl carbamate (Troc), 2-trimethylsilylethyl carbamate (Teoc), 2-phenylethyl carbamate (hZ), 1-(1-adamantyl)-1-methylethyl carbamate (Adpoc), 1,1-dimethyl-2-haloethyl carbamate, 1,1-dimethyl-2,2-dibromoethyl carbamate (DB-t-BOC), 1,1-dimethyl-2,2,2-trichloroethyl carbamate (TCBOC), 1-methyl-1-(4-biphenylypethyl carbamate (Bpoc), 1-(3,5-ditbutylphenyl)-1-methylethyl carbamate (t-Bumeoc), 2-(2'- and 4'-pyridyl)ethyl carbamate (Pyoc), 2-(N,N-dicyclohexylcarboxamido)ethyl carbamate, t-butyl carbamate (BOC), 1-adamantyl carbamate (Adoc), vinyl carbamate (Voc), allyl carbamate (Alloc), 1-isopropylallyl carbamate (Ipaoc), cinnamyl carbamate (Coc), 4-nitrocinnamyl carbamate (Noc), 8-quinolyl carbamate, N-hydroxypiperidinyl carbamate, alkyldithio carbamate, benzyl carbamate (Cbz), p-methoxybenzyl carbamate (Moz), p-nitrobenzyl carbamate, p-bromobenzyl carbamate, p-chlorobenzyl carbamate, 2,4-dichlorobenzyl carbamate, 4-methylsulfinylbenzyl carbamate (Msz), 9-anthrylmethyl carbamate, diphenylmethyl carbamate, 2-methylthioethyl carbamate, 2-methylsulfonylethyl carbamate, 2-(p-toluenesulfonypethyl carbamate, [2-(1,3-dithianyl)]methyl carbamate (Dmoc), 4-methylthiophenyl carbamate (Mtpc), 2,4-dimethylthiophenyl carbamate (Bmpc), 2-phosphonioethyl carbamate (Peoc), 2-triphenylphosphonioisopropyl carbamate (Ppoc), 1,1-dimethyl-2-cyanoethyl carbamate, m-chloro-p-acyloxybenzyl carbamate, p-(dihydroxyboryl)benzyl carbamate, 5-benzisoxazolylmethyl carbamate, 2-(trifluoromethyl)-6-chromonylmethyl carbamate (Tcroc), m-nitrophenyl carbamate, 3,5-dimethoxybenzyl carbamate, o-nitrobenzyl carbamate, 3,4-dimethoxy-6-nitrobenzyl carbamate, phenyl(o-nitrophenyl)methyl carbamate, t-amyl carbamate, S-benzyl thiocarbamate, p-cyanobenzyl carbamate, cyclobutyl carbamate, cyclohexyl carbamate, cyclopentyl carbamate, cyclopropylmethyl carbamate, p-decyloxybenzyl carbamate, 2,2-dimethoxyacylvinyl carbamate, o-(N, N-dimethylcarboxamido)benzyl carbamate, 1,1-dimethyl-3-(N,N-dimethylcarboxamido)propyl carbamate, 1,1-dimethylpropynyl carbamate, di(2-pyridyl)methyl carbamate, 2-furanylmethyl carbamate, 2-iodoethyl carbamate, isobornyl carbamate, isobutyl carbamate, isonicotinyl carbamate, p-(p'-methoxyphenylazo)benzyl carbamate, 1-methylcyclobutyl carbamate, 1-methylcyclohexyl carbamate, 1-methyllcyclopropylmethyl carbamate, 1-methyl-1-(3,5-dimethoxyphenypethyl carbamate, 1-methyl-1-(p-phenylazophenypethyl carbamate, 1-methyl-1-phenylethyl carbamate, 1-methyl-1-(4-pyridypethyl carbamate, phenyl carbamate, p-(phenylazo)benzyl carbamate, 2,4,6-tritbutylphenyl carbamate, 4-(trimethylammonium)benzyl carbamate, and 2,4,6-trimethylbenzyl carbamate.

Nitrogen-protecting groups such as sulfonamide groups include, but are not limited to, p-toluenesulfonamide (Ts), benzenesulfonamide, 2,3,6,-trimethyl-4-methoxybenzenesulfonamid (Mtr), 2,4,6-trimethoxybenzenesulfonamide (Mtb), 2,6-dimethyl-4-methoxybenzenesulfonamide (Pme), 2,3,5,6-tetramethyl-4-methoxybenzenesulfonamide (Mte), 4-methoxybenzenesulfonamide (Mbs), 2,4,6-trimethylbenzenesulfonamide (Mts), 2,6-dimethoxy-4-methylbenzenesulfonamide (iMds), 2,2,5,7,8-pentamethylchroman-6-sulfonamide (Pmc), methanesulfonamide (Ms), β-trimethylsilylethanesulfonamide (SES), 9-anthracenesulfonamide, 4-(4',8'-dimethoxynaphthylmethyl)benzenesulfonamide (DNMBS), benzylsulfonamide, trifluoromethylsulfonamide, and phenacylsulfonamide.

Other nitrogen-protecting groups include, but are not limited to, phenothiazinyl-(10)-acyl derivative, N'-p-toluenesulfonylaminoacyl derivative, N'-phenylaminothioacyl derivative, N-benzoylphenylalanyl derivative, N-acetylmethionine derivative, 4,5-diphenyl-3-oxazolin-2-one, N-phthalimide, N-dithiasuccinimide (Dts), N-2,3-diphenylmaleimide, N-2,5-dimethylpyrrole, N-1,1,4,4-tetramethyldisilylazacyclopentane adduct (STABASE), 5-substituted 1,3-dimethyl-1,3,5-triazacyclohexan-2-one, 5-substituted 1,3dibenzyl-1,3,5-triazacyclohexan-2-one, 1-substituted 3,5-dinitro-4-pyridone, N-methylamine, N-allylamine, N-[2-(trimethylsilyl)ethoxy]methylamine (SEM), N-3-acetoxypropylamine, N-(1-isopropyl-4-nitro-2-oxo-3-pyroolin-3-yl)amine, quaternary ammonium salts, N-benzylamine, N-di-(4-methoxyphenyl)methylamine, N-5-dibenzosuberylamine, N-triphenylmethylamine (Tr), N-[(4-methoxyphenyl)diphenylmethyl]amine (MMTr), N-9-phenylfluorenylamine (PhF), N-2,7-dichloro-9-fluorenylmethyleneamine, N-ferrocenylmethylamino (Fcm), N-2-picolylamino N'-oxide, N-1,1-dimethylthiomethyleneamine, N-benzylideneamine, N-pmethoxybenzylideneamine, N-diphenylmethyleneamine, N-[(2-pyridyl)mesityl]methyleneamine, N-(N',N'-dimethylaminomethylene) amine, N,N'-isopropylidenediamine, N-p- nitrobenzylideneamine, N-salicylideneamine, N-5-chlorosalicylideneamine, N-(5-chloro-2-hydroxyphenyl)phenylmethyleneamine, N-cyclohexylideneamine, N-(5,5-dimethyl-3-oxo-1-cyclohexenyl)amine, N-borane derivative, N-diphenylborinic acid derivative, N-[phenyl(pentaacylchromium- or tungsten)acyl]amine, N-copper chelate, N-zinc chelate, N-nitroamine, N-nitrosoamine, amine N-oxide, diphenylphosphinamide (Dpp), dimethylthiophosphinamide (Mpt), diphenylthiophosphinamide (Ppt), dialkyl phosphoramidates, dibenzyl phosphoramidate, diphenyl phosphoramidate, benzenesulfenamide, o-nitrobenzenesulfenamide (Nps), 2,4-dinitrobenzenesulfenamide, pentachlorobenzenesulfenamide, 2-nitro-4-methoxybenzenesulfenamide, triphenylmethylsulfenamide, and 3-nitropyridinesulfenamide (Npys).

It will be appreciated that the above groups and/or compounds, as described herein, may be optionally substituted with any number of substituents or functional moieties. That is, any of the above groups may be optionally substituted. As used herein, the term "substituted" is contemplated to include all permissible substituents of organic compounds, "permissible" being in the context of the chemical rules of valence known to those of ordinary skill in the art. In general, the term "substituted" whether preceded by the term "optionally" or not, and substituents contained in formulas of this invention, refer to the replacement of hydrogen radicals in a given structure with the radical of a specified substituent. When more than one position in any given structure may be substituted with more than one substituent selected from a specified group, the substituent may be either the same or different at every position. It will be understood that "substituted" also includes that the substitution results in a stable compound, e.g., which does not spontaneously undergo transformation such as by rearrangement, cyclization, elimination, etc. In some cases, "substituted" may generally refer to replacement of a hydrogen with a substituent as described herein. However, "substituted," as used herein, does not encompass replacement and/or alteration of a key functional group by which a molecule is identified, e.g., such that the "substituted" functional group becomes, through substitution, a different functional group. For example, a "substituted phenyl group" must still comprise the phenyl moiety and cannot be modified by substitution, in this definition, to become, e.g., a pyridine ring. In a broad aspect, the permissible substituents include acyclic and cyclic, branched and unbranched, carbocyclic and heterocyclic, aromatic and nonaromatic substituents of organic compounds. Illustrative substituents include, for example, those described herein. The permissible substituents can be one or more and the same or different for appropriate organic compounds. For purposes of this invention, the heteroatoms such as nitrogen may have hydrogen substituents and/or any permissible substituents of organic compounds described herein which satisfy the valencies of the heteroatoms. Furthermore, this invention is not intended to be limited in any manner by the permissible substituents of organic compounds. The term "stable," as used herein, preferably refers to compounds which possess stability sufficient to allow manufacture and which maintain the integrity of the compound for a sufficient period of time to be detected and preferably for a sufficient period of time to be useful for the purposes detailed herein.

Examples of substituents include, but are not limited to, halogen, azide, alkyl, aralkyl, alkenyl, alkynyl, cycloalkyl, hydroxyl, alkoxyl, amino, nitro, sulfhydryl, imino, amido, phosphonate, phosphinate, carbonyl, carboxyl, silyl, ether, alkylthio, sulfonyl, sulfonamido, ketone, aldehyde, ester, heterocyclyl, aromatic or heteroaromatic moieties, $—CF_3$, $—CN$, aryl, aryloxy, perhaloalkoxy, aralkoxy, heteroaryl, heteroaryloxy, heteroarylalkyl, heteroaralkoxy, azido, amino, halide, alkylthio, oxo, acylalkyl, carboxy esters, -carboxamido, acyloxy, aminoalkyl, alkylaminoaryl, alkylaryl, alkylaminoalkyl, alkoxyaryl, arylamino, aralkylamino, alkylsulfonyl, -carboxamidoalkylaryl, -carboxamidoaryl, hydroxyalkyl, haloalkyl, alkylaminoalkylcarboxy-, aminocarboxamidoalkyl-, cyano, alkoxyalkyl, perhaloalkyl, arylalkyloxyalkyl, and the like.

The following examples are intended to illustrate certain embodiments of the present invention, but do not exemplify the full scope of the invention.

EXAMPLES

Example 1

Post-synthetic ion exchange of $Co(CO)_4^-$ into a Cr-MIL-101 metal organic framework was effectively carried out for the formation of a heterogeneous [Lewis acid]$^+$[Co(CO)$_4$]$^-$ system. The charge-balancing $F^-$ anions in the as-synthesized Cr-MIL-101 were directly coordinated to the Cr(III) sites of the framework. To replace these framework-bound anions with uncoordinated $Co(CO)_4^-$, anion exchange was performed in two discrete steps: (1) exchange of the bound $F^-$ with mobile $Cl^-$ using $AlCl_3$ and (2) exchange of the mobile $Cl^-$ with $Co(CO)_4^-$ using $Na[Co(CO)_4]$. In the initial anion exchange, $Al^{3+}$ shows greater affinity to $F^-$ than the framework Cr(III) sites, resulting in the abstraction of $F^-$ from the MOF. The consequent charge imbalance was compensated by the inclusion of $Cl^-$ into the framework.

Figure 7A:
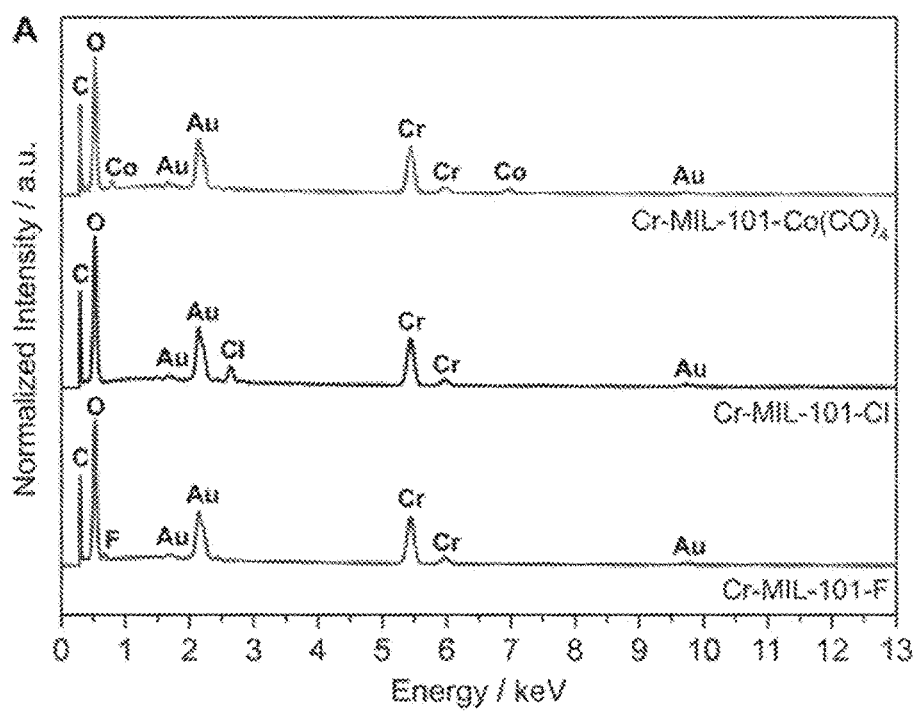
FIG. 7A and FIG. 7B each shows a graphical representation of components in the formation of a metal organic framework, according to one or more non-limiting embodiments.

This sequence of events was tracked by energy dispersive X-ray spectroscopy (EDX) analysis of the Cr-MIL-101 sample before (Cr-MIL-101-F) and after (Cr-MIL-101-Cl) soaking in a solution of $AlCl_3$ (as shown in FIG. 7A). In the EDX spectra, the F K$\alpha$ peak observed at 0.68 keV for Cr-MIL-101-F was replaced by the Cl K$\alpha$ peak at 2.62 keV for Cr-MIL-101-Cl upon $AlCl_3$ treatment and extensive washing. The absence of the F K$\alpha$ and Al K$\alpha$ peaks in the spectrum of Cr-MIL-101-Cl implied a complete exchange of $F^-$ by $Cl^-$ and a negligible retention of the unreacted $AlCl_3$. The structure of the MOF remained intact after the ion exchange as evidenced by the retention of crystallinity in the powder X-ray diffraction (PXRD) analysis of Cr-MIL-101-Cl.

Figure 7B:
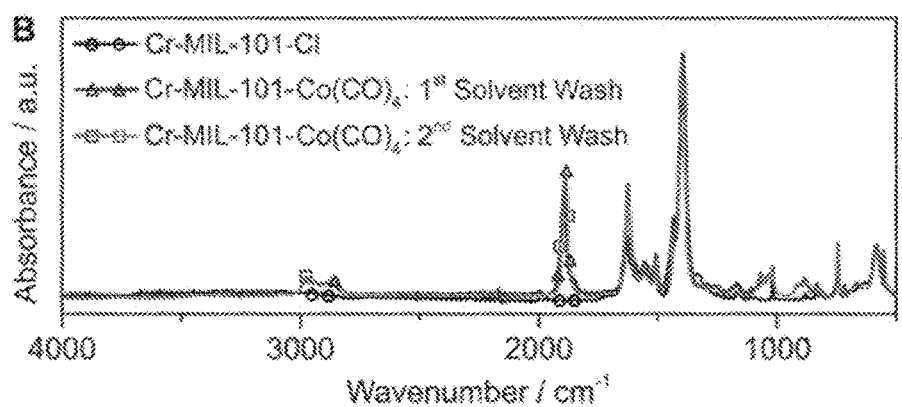

Subsequent anion exchange between Cr-MIL-101-Cl and Na[Co(CO)$_4$] was analyzed by EDX and attenuated total reflectance infrared spectroscopy (ATR-IR), both of which confirmed the inclusion of $Co(CO)_4^-$ into the framework. The Cl K$\alpha$ peak in the EDX spectrum of Cr-MIL-101-Cl was replaced by the Co K$\alpha$ peak at 6.92 keV and the Co L$\alpha$ peak at 0.78 keV upon soaking the sample in a Na[Co(CO)$_4$] solution (as shown in FIG. 7A). The Co peaks persisted even after repeatedly washing Cr-MIL-101 in tetrahydrofuran (THF), which readily solubilizes Na[Co(CO)$_4$]. It is also clear that the Cl K$\alpha$ peak at 2.62 keV and the Na K$\alpha$ peak at 1.04 keV are nearly absent in the EDX spectrum of Cr-MIL-101-Co(CO)$_4$, whereas these peaks are clearly present in the spectra of Cr-MIL-101-Cl and Na[Co(CO)$_4$], respectively. These observations suggest that the observed Co signal for Cr-MIL-101-Co(CO)$_4$ does not stem from residual Na[Co(CO)$_4$] adsorbed on the surface of the MOF, but rather from substitution of $Cl^-$ by $Co(CO)_4^-$. This ion exchange is further corroborated by the ATR-IR absorption spectrum of Cr-MIL-101-Co(CO)$_4$, which clearly shows the emergence of a single peak at 1888 cm$^{-1}$ after the exchange procedure (as shown in FIG. 7B). This band corresponds very well to the characteristic carbonyl stretch band of the tetrahedral Co(CO)$_4^-$ ion in various metal complexes, including those reported for the homogeneous [Lewis acid]$^+$[Co(CO)$_4$]$^-$ epoxide carbonylation catalysts. The porous structure of the MOF was also retained after this final ion exchange step as evident in the unchanged PXRD pattern for Cr-MIL-101-CO(CO)$_4$.

Example 2

The catalytic activity of Cr-MIL-101-Co(CO)$_4$ for the ring-expanding carbonylation of epoxides was tested and found to be commensurate with that of homogeneous catalysts. When using neat 1,2-epoxyhexane as a substrate, Cr-MIL-101-Co(CO)$_4$ loaded at 0.5 cobalt mol % produced the corresponding β-lactone product with 86% yield in 5 h under 60 bar of CO at 60° C. (Table 1, entry 1). This led to a calculated site time yield (STY) of 34 h$^{-1}$, which is comparable to the values reported for a series of homogeneous catalysts under similar reaction conditions. The solvent dependence of the carbonylation activity in Cr-MIL-101-Co(CO)$_4$ also mimicked that of reported homogeneous systems. When a range of solvents was screened for optimal activity with Cr-MIL-101-Co(CO)$_4$, reactions in weakly coordinating ethers such as 1,2-dimethoxyethane (DME) showed the highest activity. In other solvents, especially the more strongly coordinating solvents such as THF, the reactions proceeded at a much slower rate. Identical solvent dependence has been reported for the Cr(III)-based [(salph)Cr(THF)$_2$]$^+$[Co(CO)$_4$]$^-$ (salph=N,N'-o-phenylenebis-(3,5-di-tert-butyl-salicylideneimine)), a homogeneous catalyst used in the formation of β-lactone. Importantly, Cr-MIL-101-Co(CO)$_4$ also displayed the broad functional group tolerance of the homogeneous catalysts, as evidenced by its activity toward an array of aliphatic epoxides as well as glycidyl ether and epichlorohydrin (Table 1, entries 2-5).

resumed its epoxide carbonylation activity. The structural integrity of Cr-MIL-101-Co(CO)$_4$ was also retained after all epoxide carbonylation reactions, as confirmed by the PXRD analysis of Cr-MIL-101-Co(CO)$_4$ after a catalytic run. For a verification of the catalytic cooperativity between the Cr(III) sites and Co(CO)$_4^-$ in Cr-MIL-101-Co(CO)$_4$, Cr-MIL-101-F, Cr-MIL-101-Cl, and Na[Co(CO)$_4$] were tested for epoxide carbonylation activity. All systems displayed <2% product formation when subjected to a 5 h reaction with neat 1,2-epoxyhexane at 0.5 mol % loading, 60 bar CO, and 60° C. In addition, no appreciable catalytic activity was observed when HKUST-1 (Cu$_3$BTC$_2$, H$_3$BTC=benzene-1,3,5-tri-carboxylic acid), a representative Lewis acidic MOF with Cu(II) sites, was subjected to the same reaction conditions along with an equimolar amount of Na[Co(CO)$_4$]. These results show that the epoxide carbonylation activity is unique to Cr-MIL-101-Co(CO)$_4$, where the specific combination of Co(CO)$_4^-$ and the Lewis acidic Cr(III) sites of the Cr-MIL-101 framework is required for cooperative catalysis.

Example 3

Example 3 demonstrates a process for forming the MOF, Cr-MIL-101. A typical synthesis involved a mixture of Cr(NO$_3$)$_3$·9H$_2$O (800 mg, 2.00 mmol) and terephthalic acid (332 mg, 2.00 mmol) in 10.0 ml of water with 2.0 mmol of HF. The mixture was introduced to a Parr pressure vessel, which was placed in a convection oven held at 220° C. for 8 h. After natural cooling, the mixture was first passed through a large-pore fritted glass filter to remove the residual terephthalic acid. The filtrate was then passed through a fine-pore filter paper to collect the Cr-MIL-101 product. The obtained Cr-MIL-101 was further purified by two solvent treatments using ethanol and aqueous NH$_4$F. The first solvent treatment involved introducing the solid sample to

TABLE 1

Catalysts for the Ring-expansion Carbonylation of Epoxides

| Entry | Catalyst | R | R' | Solvent | P$_{CO}$ (bar) | T (° C.) | t (h) | [Epoxide]/[Co]$^a$ | Yield (%) | STY (h$^{-1}$)$^b$ |
|---|---|---|---|---|---|---|---|---|---|---|
| 1 | Cr-MIL-101-Co(CO)$_4$ | n-Bu | H | neat | 60 | 60 | 5 | 200$^i$ | 86$^k$ | 34 |
| 2 | Cr-MIL-101-Co(CO)$_4$ | n-Bu | H | DME$^h$ | 60 | 60 | 1 | 200$^i$ | 88$^k$ | 180 |
| 3 | Cr-MIL-101-Co(CO)$_4$ | (CH$_2$)$_2$HC=CH$_2$ | H | DME$^h$ | 60 | 60 | 1.5 | 200$^i$ | 93$^k$ | 120 |
| 4 | Cr-MIL-101-Co(CO)$_4$ | CH$_2$OEt | H | DME$^h$ | 60 | 60 | 4 | 200$^i$ | 92$^k$ | 46 |
| 5 | Cr-MIL-101-Co(CO)$_4$ | CH$_2$Cl | H | DME$^h$ | 60 | 60 | 4 | 200$^i$ | 56$^k$ | 28 |

$^a$[Epoxide]/[Co] = moles of epoxide per mole of cobalt in catalyst.
$^b$Site Time Yield = moles of β-lactone produced per mole of cobalt in catalyst per hour throughout overall reaction time t.
$^h$DME = 1,2-dimethoxyethane.
$^i$As calculated from the inductively coupled plasma mass spectrometry (ICP-MS) derived cobalt content of the catalyst.
$^j$Isolated yield.
$^k$As determined by $^1$H-NMR analysis.

To validate the heterogeneous nature of the observed catalytic activity, Cr-MIL-101-Co(CO)$_4$ was filtered off from a portion of the epoxide carbonylation reaction mixture at 15% conversion. When the acquired filtrate and the unfiltered mixture were both subjected to the standard reaction conditions again, the filtrate did not show any increase in β-lactone yield whereas the unfiltered portion refluxing ethanol until no detection of colored impurities in the mother liquor. The sample was then subjected to an aqueous solution of 30 mM NH$_4$F at 60° C. for 10 h (150 ml of solution/1 g of sample). After natural cooling, Cr-MIL-101 was filtered and washed several times with hot water at 60° C. (150 ml of water/1 g of sample) to remove residual $NH_4F$. The filtered sample was then desolvated by heating under vacuum at 150° C. for 18 h.

Example 4

Example 4 demonstrates an exemplary process for providing anion exchange between Cr-MIL-101 and $AlCl_3$. A typical procedure involved subjecting Cr-MIL-101 to an aqueous solution of 30 mM $AlCl_3.6H_2O$ at 90° C. for 18 h (100 ml of solution/100 mg of sample). The solid sample was filtered and washed several times with hot water at 90° C. to remove residual $AlCl_3$. The filtered sample was then desolvated by heating under vacuum at 150° C. for 18 h. The obtained final product was labeled as Cr-MIL-101-Cl.

Example 5

Example 5 demonstrates an exemplary process for preparing $Na[Co(CO)_4]$. A typical synthesis involved a Schlenk flask charged with $Co_2(CO)_8$ (5.00 g, 14.6 mmol) and a magnetic stir bar under an inert atmosphere. NaOH (6.00 g, 150 mmol) and tetrahydrofuran (50 ml) were then transferred to the flask and the reaction mixture was left to stir in an ice bath for 6 h while wrapped in aluminum foil. The product mixture was passed through a Celite pad and washed several times with tetrahydrofuran. The collected filtrate was pumped down and dried overnight to obtain the final product.

Example 6

Example 6 demonstrates an exemplary process for providing anion exchange of Cr-MIL-101-Cl with $Na[Co(CO)_4]$. A typical procedure involved subjecting Cr-MIL-101-Cl to a methanol solution of 30 mM $Na[Co(CO)_4]$ and stirring overnight (100 ml solution/100 mg of Cr-MIL-101-Cl). The solid sample was then filtered and washed by suspending the sample in fresh tetrahydrofuran (100 ml/100 mg sample) and stirring overnight. The washing procedure was repeated several times. The obtained final product was labeled as $Cr-MIL-101-Co(CO)_4$.

Example 7

Example 7 demonstrates an exemplary process for epoxide carbonylation with $Cr-MIL-101-Co(CO)_4$. A typical procedure involved charging a glass vial with epoxide (~200 mg), 1,2-dimethoxyethane (1 ml/1 mmol of epoxide), $Cr-MIL-101-Co(CO)_4$ (0.5 cobalt mol % loading with respect to the epoxide, based on the ICP-MS derived cobalt content of $Cr-MIL-101-Co(CO)_4$), and a magnetic stir bar. The vial was then immediately transferred to a stainless steel Parr reactor, and the reactor was sealed in an inert-atmosphere glove box. The reactor was then placed in a hood, pressurized with CO, and heated to 60° C. (CO pressure of 60 bar at 60° C.). The temperature was held constant while stirring for the specified time, after which the reactor was cooled in a dry ice or an ice bath until the pressure reached a minimum. After careful venting of CO to atmospheric pressure, the glass vial was removed, and the product mixture was filtered through a 0.2 μm polytetrafluoroethylene syringe filter. A small sample of the filtrate was analyzed via $^1$H-NMR and/or gas chromatography with added mesitylene as a standard. Larger amount of epoxide (~2.00 g) was used for neat epoxide reactions. All control reactions were conducted in an analogous manner as described above for $Cr-MIL-101-Co(CO)_4$.

Example 8

Example 8 demonstrates an exemplary process for β-lactone carbonylation with $Cr-MIL-101-Co(CO)_4$. A typical procedure involved charging a glass vial with toluene (2 ml/1 mmol of β-lactone), $Cr-MIL-101-Co(CO)_4$ (1 cobalt mol % loading with respect to the β-lactone, based on the ICP-MS derived cobalt content of $Cr-MIL-101-Co(CO)_4$), and a magnetic stir bar. The vial was then immediately transferred to a stainless steel Parr reactor, and the reactor was sealed in an inert-atmosphere glove box. The reactor was then placed in a hood, pressurized with CO to 30 bar and heated to 40° C. with stirring. After ~20 min. the reactor was slowly vented to atmospheric pressure, after which the reactant β-lactone (~100 mg) was added to the Parr reactor via a rubber septum syringe inlet. The reactor was then pressurized with CO to 60 bar and heated to 80° C. with stirring (CO pressure of 60 bar at 80° C.). The temperature was held constant while stirring for the specified time, after which the reactor was cooled in a dry ice or an ice bath until the pressure reached a minimum. After careful venting of CO to atmospheric pressure, the glass vial was removed, and the product mixture was filtered through a 0.2 μm polytetrafluoroethylene syringe filter. A small sample of the filtrate was analyzed via $^1$H-NMR and/or gas chromatography with added mesitylene as a standard. All control reactions were conducted in an analogous manner as described above for $Cr-MIL-101-CO(CO)_4$.

Example 9

Example 9 demonstrates an exemplary process for testing catalyst heterogeneity with $Cr-MIL-101-Co(CO)_4$. A typical procedure involved conducting a standard epoxide carbonylation reaction as outlined above for a sufficient time to reach the desired conversion of the substrate epoxide. After the reaction, the Parr reactor was carefully vented to atmospheric pressure, refilled with nitrogen, and brought into an inert-atmosphere glove box. The glass vial holding the reaction mixture was then taken out of the reactor and the reaction mixture was divided into two equal aliquots. One of the aliquots was passed through a 0.2 μm polytetrafluoroethylene syringe filter to collect the filtrate in a separate vial. A small fraction of the filtrate was analyzed via gas chromatography with added mesitylene as a standard. The two glass vials, one holding the collected filtrate and the other holding the unfiltered reaction mixture, were transferred to separate Parr reactors, and the reactors were sealed in the glove box. The two reactors were then placed in a hood and again subjected to standard reaction conditions. After the specified time, the product mixtures from both reactors were recovered and analyzed in a manner analogous to the procedure outlined above for the standard epoxide carbonylation reaction.

While several embodiments of the present invention have been described and illustrated herein, those of ordinary skill in the art will readily envision a variety of other means and/or structures for performing the functions and/or obtaining the results and/or one or more of the advantages described herein, and each of such variations and/or modifications is deemed to be within the scope of the present invention. More generally, those skilled in the art will readily appreciate that all parameters, dimensions, materials, and configurations described herein are meant to be exemplary and that the actual parameters, dimensions, materials, and/or configurations will depend upon the specific application or applications for which the teachings of the present invention is/are used. Those skilled in the art will recognize, or be able to ascertain using no more than routine experimentation, many equivalents to the specific embodiments of the invention described herein. It is, therefore, to be understood that the foregoing embodiments are presented by way of example only and that, within the scope of the appended claims and equivalents thereto, the invention may be practiced otherwise than as specifically described and claimed. The present invention is directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the scope of the present invention.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Other elements may optionally be present other than the elements specifically identified by the "and/or" clause, whether related or unrelated to those elements specifically identified unless clearly indicated to the contrary. Thus, as a non-limiting example, a reference to "A and/or B," when used in conjunction with open-ended language such as "comprising" can refer, in one embodiment, to A without B (optionally including elements other than B); in another embodiment, to B without A (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of." "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

In the claims, as well as in the specification above, all transitional phrases such as "comprising," "including," "carrying," "having," "containing," "involving," "holding," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

What is claimed is:

1. A composition, comprising:
a metal organic framework compound comprising a plurality of metal ions, each coordinated with at least one ligand; and
a plurality of Co(CO)$_4^-$ anions associated with at least a portion of the metal ions.

2. A method of synthesizing a composition, comprising:
exposing a metal organic framework (MOF) comprising a plurality of metal ions, each coordinated with at least one ligand, to a solution comprising a plurality of Co(CO)$_4^-$ anions, thereby forming a composition comprising the MOF having at least a portion of the metal ions associated with a Co(CO)$_4^-$ anion.

3. A method, comprising:
exposing carbon monoxide and an epoxide substrate having the formula,

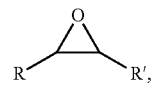

to the composition of claim 1, thereby forming a β-lactone having the formula,

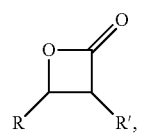

wherein R and R' are the same or different and are hydrogen, an optionally substituted aliphatic group, an optionally substituted heteroaliphatic group, or an optionally substituted aromatic groups, or R and R' join to form an optionally substituted alicyclic compound.

4. A method comprising,
exposing carbon monoxide and an epoxide substrate having the formula,

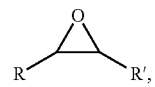

to a composition comprising a metal organic framework compound comprising a plurality of metal ions, each coordinated with at least one ligand, and a plurality of Co(CO)$_4^-$ anions associated with at least a portion of the metal ions, thereby forming a β-lactone having the formula,

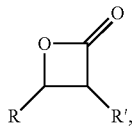

wherein R and R' are the same or different and are hydrogen, an optionally substituted aliphatic group, an optionally substituted heteroaliphatic group, or an optionally substituted aromatic groups, or R and R' join to form an optionally substituted alicyclic compound; and forming a product having the formula,

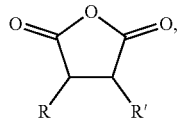

from the β-lactone having the formula,

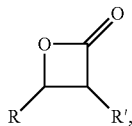

upon further exposure to the composition, wherein the product is formed with a selectivity of at least about 50%.

5. A method, comprising:
exposing carbon monoxide and a β-lactone having the formula,

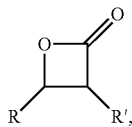

to a composition comprising a metal organic framework compound comprising a plurality of metal ions, each coordinated with at least one ligand, and a plurality of Co(CO)$_4^-$ anions associated with at least a portion of the metal ions, thereby forming a product having the formula,

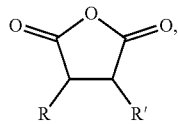

wherein R and R' are the same or different and are hydrogen, an optionally substituted aliphatic group, an optionally substituted heteroaliphatic group, or an optionally substituted aromatic groups, or R and R' join to form an optionally substituted alicyclic compound, and wherein the product is formed with a selectivity of at least about 50%.

6. The composition of claim 1, wherein the plurality of metal ions comprises Cr(III) cations.

7. The composition of claim 1, wherein the ligand comprises an aromatic group.

8. A composition comprising:
a metal organic framework compound comprising a plurality of metal ions, each coordinated with at least one ligand; and
a plurality of Co(CO)$_4^-$ anions associated with at least a portion of the metal ions, wherein the at least one ligand comprises at least one carboxylate group.

9. A composition comprising:
a metal organic framework (MOF) compound comprising a plurality of metal ions, each coordinated with at least one ligand; and
a plurality of Co(CO)$_4^-$ anions associated with at least a portion of the metal ions, wherein the MOF compound comprises Cr-MIL-101.

10. The method of claim 2, further comprising, prior to the step of exposing the MOF to the plurality of Co(CO)$_4^-$ anions:
exposing the metal organic framework to a solution to disassociate a plurality of precursor anions from the metal organic framework and to associate a plurality of intermediary anions with the metal organic framework.

11. A method of synthesizing a composition, comprising:
exposing a metal organic framework (MOF) comprising a plurality of metal ions, each coordinated with at least one ligand to a solution to disassociate a plurality of precursor anions from the metal organic framework and to associate a plurality of intermediary anions with the metal organic framework, wherein the plurality of precursor anions comprises F; and
exposing the MOF to a solution comprising a plurality of Co(CO)$_4^-$ anions, thereby forming a composition comprising the MOF having at least a portion of the metal ions associated with a Co(CO)$_4^-$ anion.

12. A method of synthesizing a composition, comprising:
exposing a metal organic framework (MOF) comprising a plurality of metal ions, each coordinated with at least one ligand to a solution to disassociate a plurality of precursor anions from the metal organic framework and to associate a plurality of intermediary anions with the metal organic framework, wherein the plurality of intermediary anions comprises Cl$^-$; and
exposing the MOF to a solution comprising a plurality of Co(CO)$_4^-$ anions, thereby forming a composition comprising the MOF having at least a portion of the metal ions associated with a Co(CO)$_4^-$ anion.

13. A method of synthesizing a composition, comprising:
exposing a metal organic framework (MOF) comprising a plurality of metal ions, each coordinated with at least one ligand to a solution to disassociate a plurality of precursor anions from the metal organic framework and to associate a plurality of intermediary anions with the metal organic framework, wherein the solution comprises AlCl$_3$; and
exposing the MOF to a solution comprising a plurality of Co(CO)$_4^-$ anions, thereby forming a composition comprising the MOF having at least a portion of the metal ions associated with a Co(CO)$_4^-$ anion.

* * * * *

UNITED STATES PATENT AND TRADEMARK OFFICE
CERTIFICATE OF CORRECTION

PATENT NO. : 11,179,708 B2  
APPLICATION NO. : 16/339688  
DATED : November 23, 2021  
INVENTOR(S) : Yuriy Román-Leshkov et al.

Page 1 of 1

It is certified that error appears in the above-identified patent and that said Letters Patent is hereby corrected as shown below:

In the Claims

At Column 32, Claim 11, Lines 33-34 please replace "wherein the plurality of precursor anions comprises F; and" with --wherein the plurality of precursor anions comprises F-; and--.

Signed and Sealed this  
First Day of March, 2022

Drew Hirshfeld  
*Performing the Functions and Duties of the*  
*Under Secretary of Commerce for Intellectual Property and*  
*Director of the United States Patent and Trademark Office*